(12) United States Patent
Betts et al.

(10) Patent No.: US 10,987,188 B2
(45) Date of Patent: Apr. 27, 2021

(54) STERILE BARRIER FOR SURGICAL LIGHTHEADS

(71) Applicants: Joshua Betts, Dublin, OH (US); Paul Witherspoon Scott, IV, San Luis Obispo, CA (US)

(72) Inventors: Joshua Betts, Dublin, OH (US); Paul Witherspoon Scott, IV, San Luis Obispo, CA (US)

( * ) Notice: Subject to any disclaimer, the term of this patent is extended or adjusted under 35 U.S.C. 154(b) by 406 days.

(21) Appl. No.: 15/478,225

(22) Filed: Apr. 3, 2017

(65) Prior Publication Data
US 2018/0280103 A1 Oct. 4, 2018

Related U.S. Application Data

(63) Continuation of application No. PCT/US2015/056272, filed on Oct. 19, 2015.

(60) Provisional application No. 62/065,671, filed on Oct. 19, 2014.

(51) Int. Cl.
*A61B 90/30* (2016.01)
*A61B 46/10* (2016.01)
*F21W 131/205* (2006.01)
*A61B 90/00* (2016.01)
(Continued)

(52) U.S. Cl.
CPC .............. *A61B 90/30* (2016.02); *A61B 46/10* (2016.02); *A61B 90/35* (2016.02); *A61B 2090/0813* (2016.02); *F21V 21/403* (2013.01); *F21W 2131/205* (2013.01)

(58) Field of Classification Search
CPC . A61B 46/10; A61B 2090/0813; A61B 90/35; A61B 90/361; A61B 90/30; A61B 50/00; A61B 2050/01–009; A61B 46/00; F21V 21/403
See application file for complete search history.

(56) References Cited

U.S. PATENT DOCUMENTS

| 3,033,359 A | 5/1962 | Mercer |
| 3,602,759 A | 8/1971 | Evans |
| 3,794,091 A | 2/1974 | Ersek |

(Continued)

FOREIGN PATENT DOCUMENTS

EP 0539315 4/1993

*Primary Examiner* — Anabel Ton

(57) ABSTRACT

An infection mitigation device providing a temporary, disposable sterile barrier between a sterile field and the non-sterile, light-emitting region of surgical lightheads. A surgical team member can easily apply and remove the protective barrier when needed. The device minimizes the opportunity for biohazardous materials from being transmitted between patients, thereby reducing the chance of infection, and ultimately providing patients with improved clinical outcomes. The center region of the barrier can be adapted to receive and/or cover (partially or completely) one or more types of centrally located surgical lighthead adjustment handles. The device can be manufactured with a unitary or composite construction. Depending on the specific composition of the barrier and application, a supportive carrier device may provide additional geometric stability for the barrier while it is maneuvered into its operational location on the lighthead. The device can be configured for compatibility will all surgical lightheads and non-OEM retrofit disposable handle systems.

11 Claims, 19 Drawing Sheets

(51) Int. Cl.
*A61B 90/35* (2016.01)
*F21V 21/40* (2006.01)

(56) References Cited

U.S. PATENT DOCUMENTS

| | | |
|---|---|---|
| 3,809,072 A | 5/1974 | Ersek |
| 3,945,044 A | 3/1976 | Mcgee |
| 4,138,746 A | 2/1979 | Bergmann |
| 4,559,671 A | 12/1985 | Andrews |
| 4,605,124 A | 8/1986 | Sandel |
| 4,643,172 A | 2/1987 | Taff |
| 4,722,296 A | 2/1988 | Bowskill |
| 4,777,574 A | 10/1988 | Eisner |
| 4,795,669 A | 1/1989 | Bowskill |
| 4,844,252 A | 7/1989 | Barron |
| 4,878,156 A | 10/1989 | Hallings |
| 4,928,211 A * | 5/1990 | Hallings ............... F21V 21/30 362/271 |
| 4,937,715 A | 6/1990 | O'shea |
| 4,974,288 A | 12/1990 | Reasner |
| 4,975,826 A | 12/1990 | Bell |
| 4,976,299 A | 12/1990 | Bickelman |
| 4,994,945 A | 2/1991 | O'shea |
| 5,036,446 A | 7/1991 | Quintanilla |
| 5,065,296 A * | 11/1991 | Cude ................... F21V 21/403 16/421 |
| 5,156,456 A | 10/1992 | Hoftman |
| 5,188,454 A | 2/1993 | Quintanilla |
| 5,273,157 A | 12/1993 | Spina |
| 5,328,368 A | 7/1994 | Kuehn |
| 5,355,292 A | 10/1994 | Hoftman |
| 5,465,461 A | 11/1995 | Sandel |
| 5,469,600 A | 11/1995 | Sandel |
| 5,493,757 A | 2/1996 | Horan |
| 5,534,346 A | 7/1996 | Robinson |
| 5,599,093 A | 2/1997 | Hoftman |
| 5,604,955 A | 2/1997 | Horan |
| 5,669,102 A | 9/1997 | Sandel |
| 5,709,465 A | 1/1998 | Lanzone |
| 5,735,598 A | 4/1998 | Ramirez |
| 5,772,316 A | 6/1998 | Hoftman |
| 5,865,621 A | 2/1999 | Calderwood |
| 5,884,996 A | 3/1999 | Cottone |
| 6,402,511 B1 | 6/2002 | Calderwood |
| 6,447,149 B1 * | 9/2002 | Kaforey ............... F21V 21/403 16/421 |
| 6,464,383 B1 | 10/2002 | Northington |
| 6,692,141 B2 | 2/2004 | Jesurun |
| 6,876,503 B1 * | 4/2005 | Weaver ............... G02B 21/0012 359/510 |
| D568,528 S | 5/2008 | Hood |
| 7,757,352 B2 | 7/2010 | Halamish |
| 8,052,339 B2 | 11/2011 | Gharibian |
| 8,752,987 B1 * | 6/2014 | Hoftman ............... A61B 46/10 362/399 |
| 10,231,799 B1 * | 3/2019 | Kalava .................. F21V 3/04 |
| 2003/0161158 A1 * | 8/2003 | Jesurun ............... A61B 46/10 362/399 |
| 2009/0133226 A1 * | 5/2009 | Halamish ............. A61B 46/10 16/421 |
| 2011/0135295 A1 * | 6/2011 | Gharibian ............. G03B 11/00 396/448 |
| 2013/0167845 A1 * | 7/2013 | Grajek ................. A61B 6/00 128/856 |
| 2014/0261456 A1 * | 9/2014 | Malackowski ........ A61B 34/20 128/849 |
| 2014/0338676 A1 * | 11/2014 | Marinchak ........... A61B 50/30 128/855 |
| 2016/0095756 A1 * | 4/2016 | Zurovcik .............. B32B 3/266 602/52 |
| 2016/0242630 A1 * | 8/2016 | Gharibian ............. A61B 46/10 |
| 2017/0231706 A1 * | 8/2017 | Vayser ................. A61B 5/0077 600/476 |
| 2018/0340579 A1 * | 11/2018 | Plante .................. F16D 37/008 |
| 2019/0290378 A1 * | 9/2019 | Schwagli .............. A61B 34/10 |
| 2019/0298471 A1 * | 10/2019 | Holop .................. A61B 34/00 |
| 2020/0046207 A1 * | 2/2020 | Calavrezos ........... A61B 46/10 |

* cited by examiner

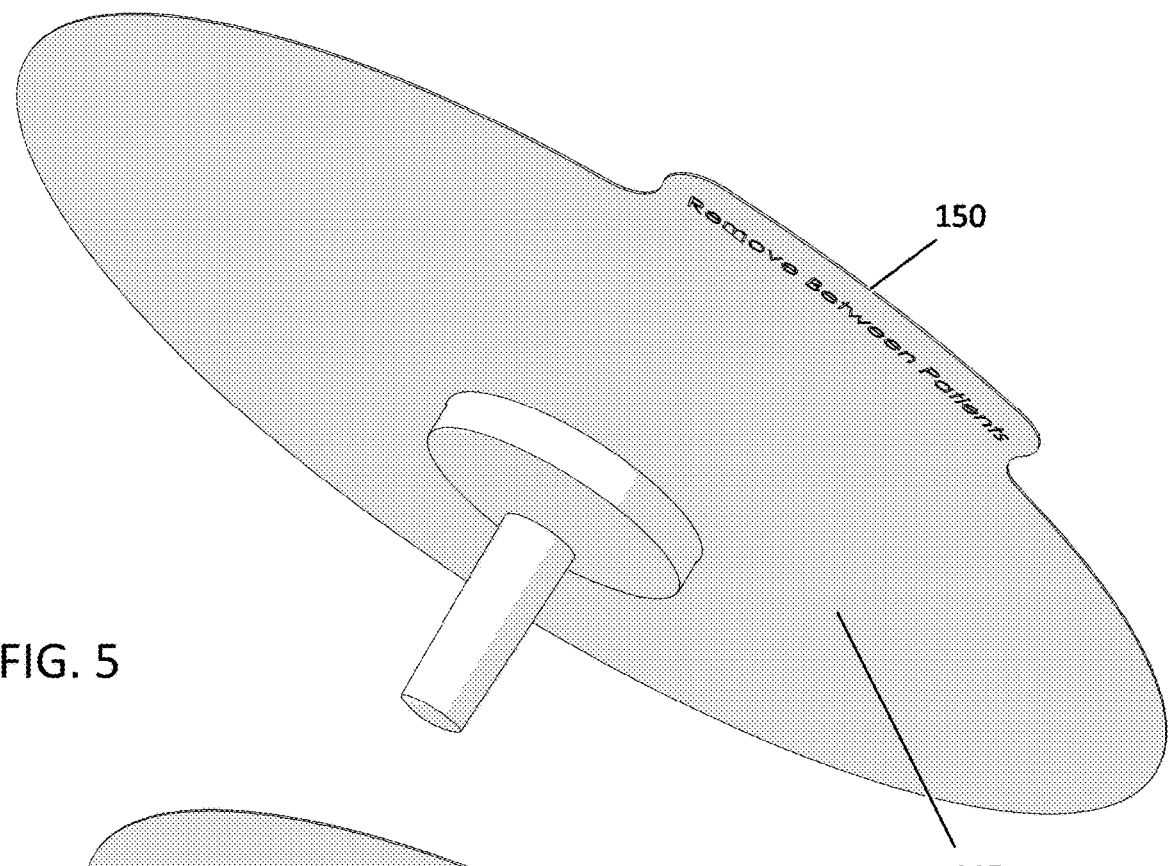
FIG. 5
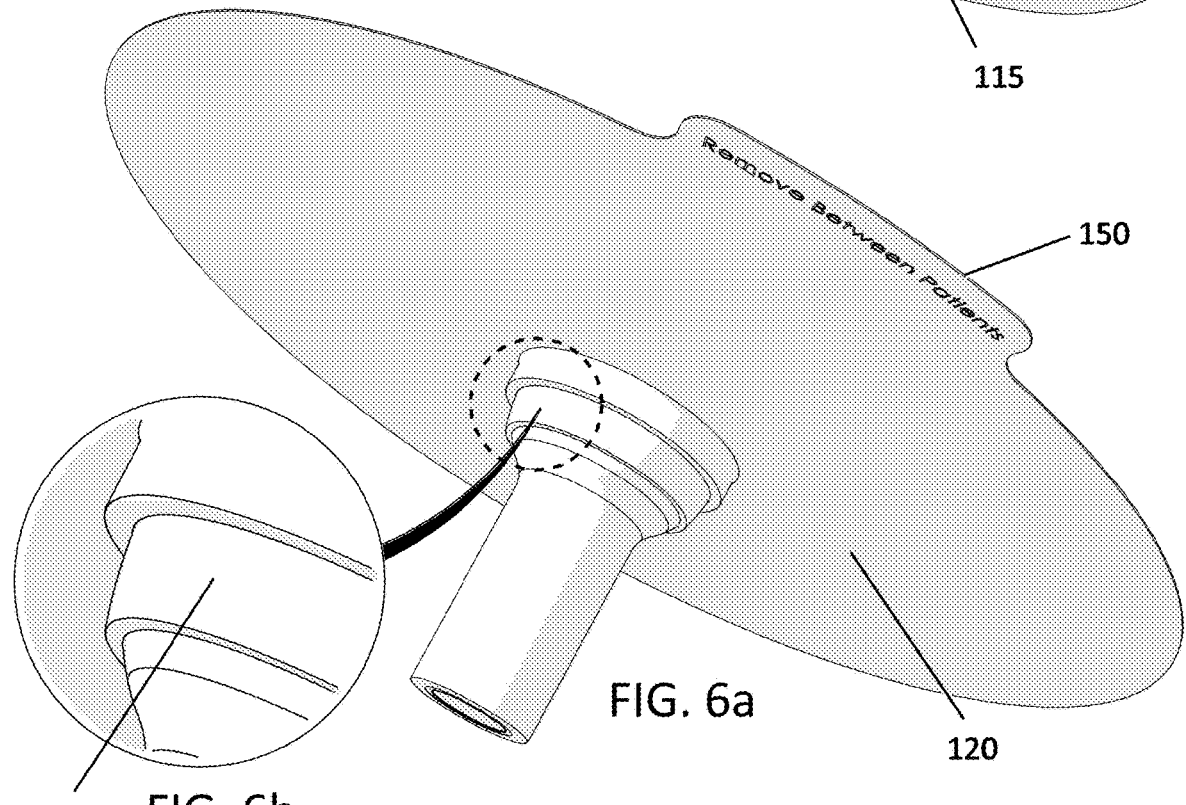
FIG. 6a
FIG. 6b

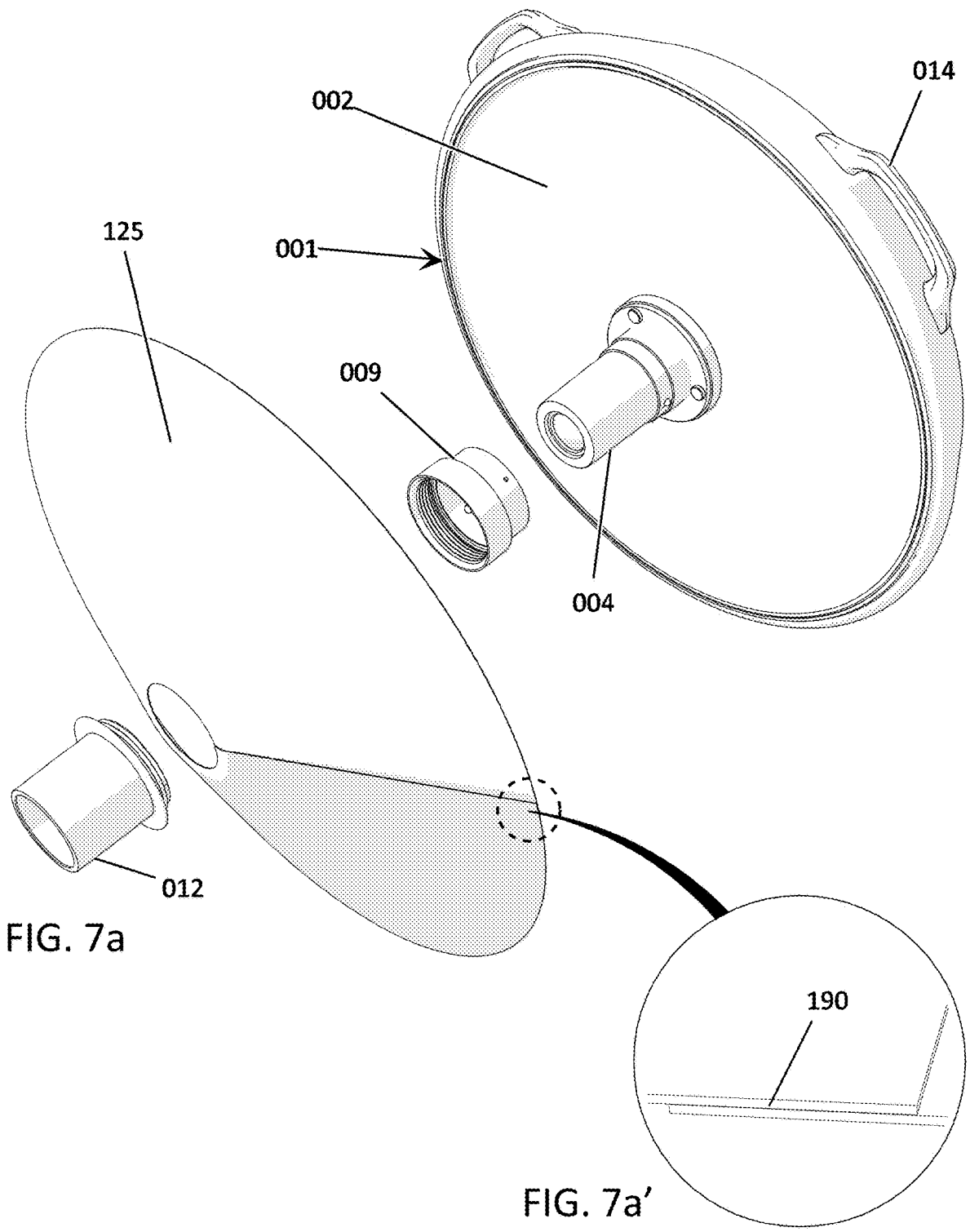

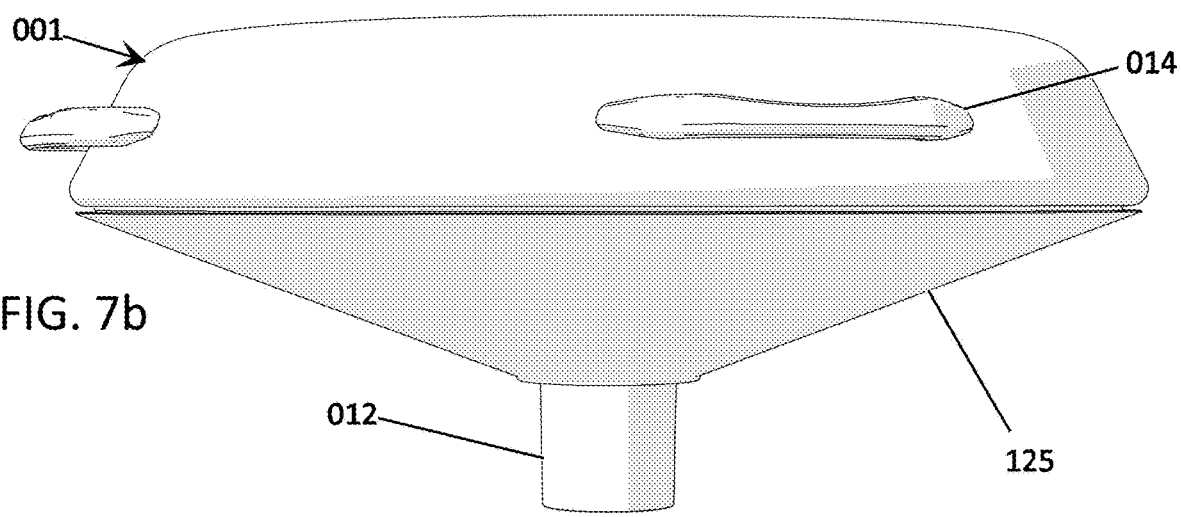
FIG. 7b
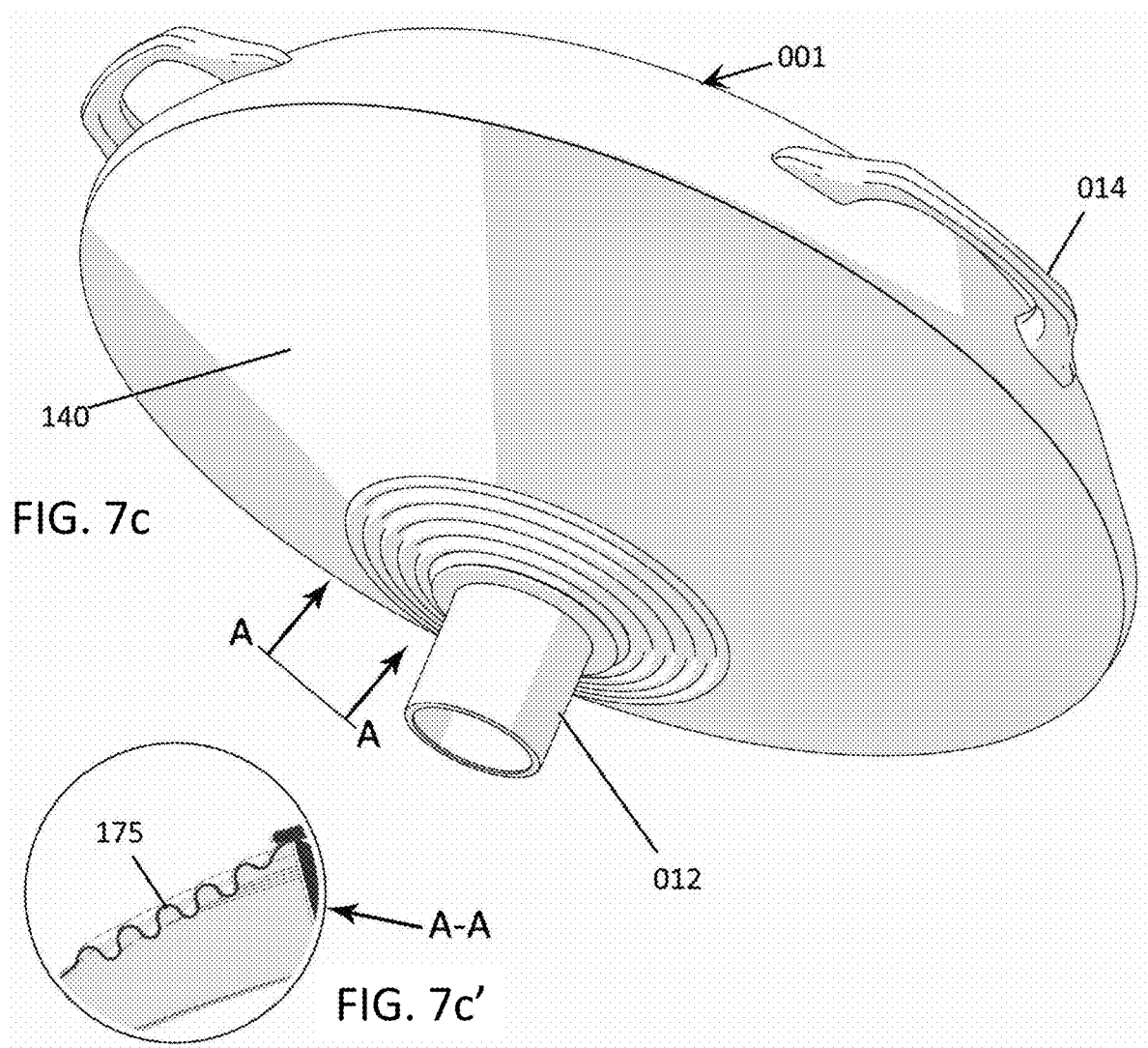
FIG. 7c
FIG. 7c'

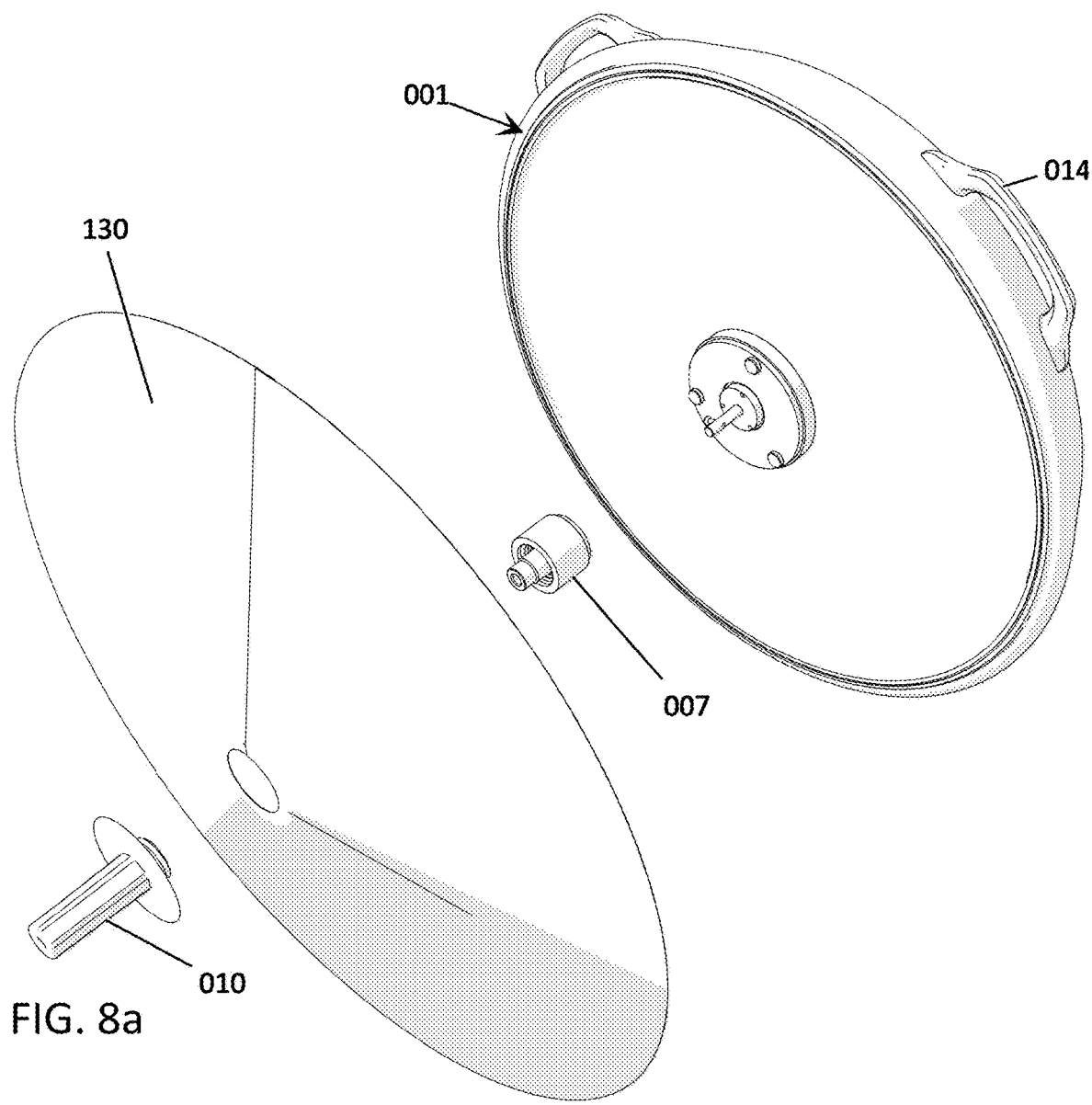
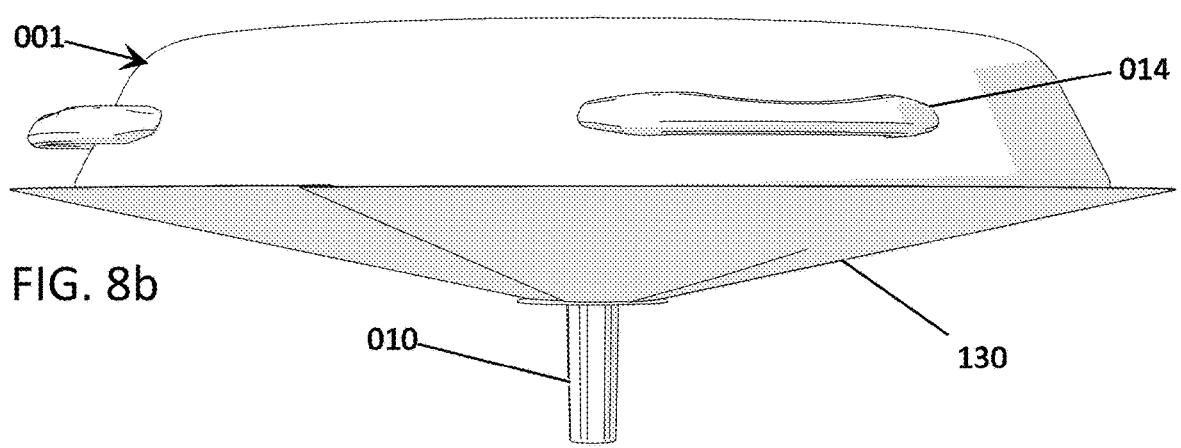

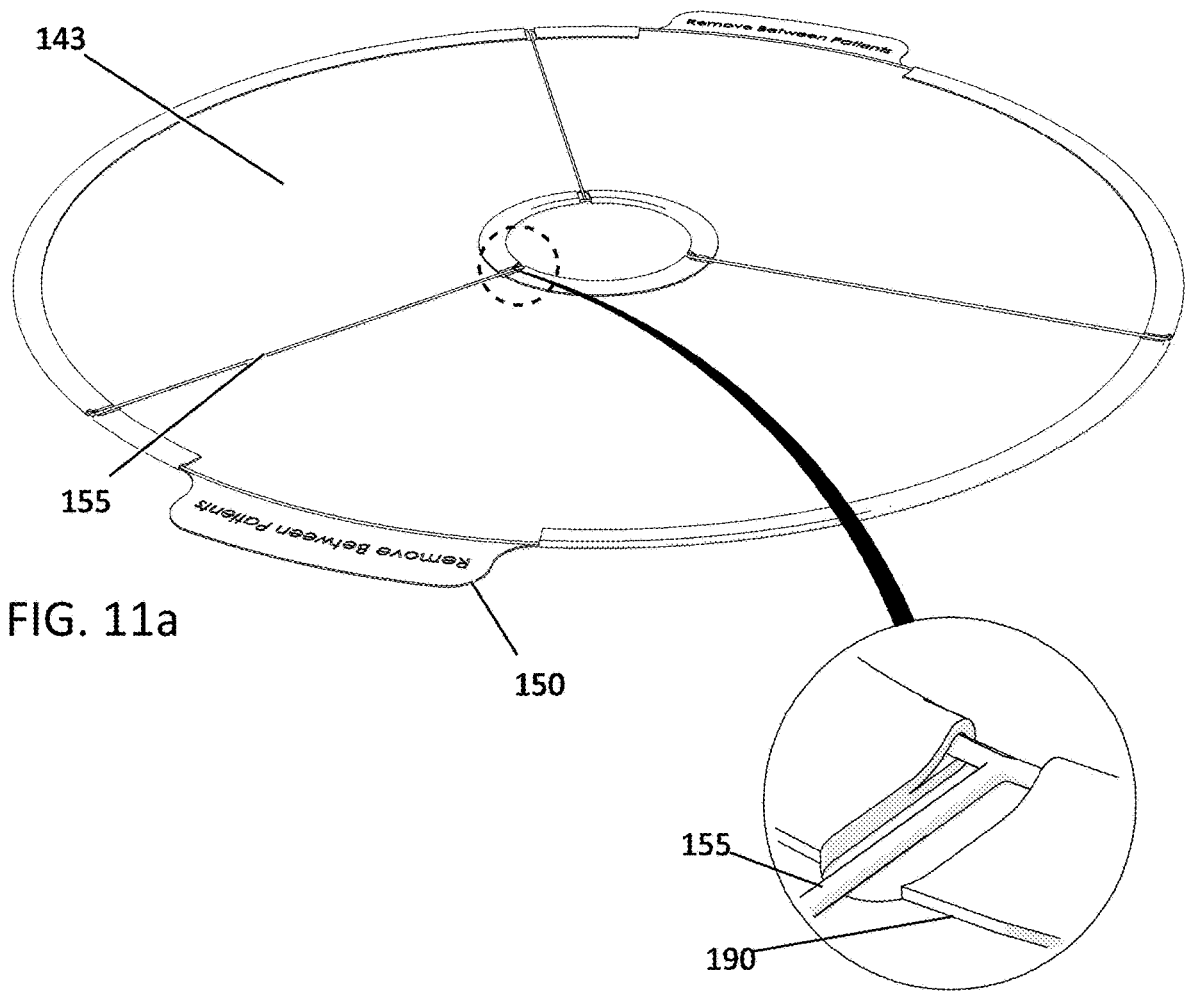

STERILE BARRIER FOR SURGICAL LIGHTHEADS

CROSS-REFERENCE TO RELATED APPLICATION

This application is a continuation of International Patent Application No. PCT/US2015/056272 filed Oct. 19, 2015, which claims the benefit of U.S. Provisional Application No. 62/065,671, filed Oct. 19, 2014, each of which is incorporated by reference herein in its entirety.

BACKGROUND

Technical Field

The disclosed device and methods relate to overhead surgical lighting systems, and more specifically, to disposable, temporary sterile barriers to shield the forward-facing regions thereof against potential biohazardous contamination.

Summary of the Art

Healthcare associated infections (HAIs) result in a significant cause of morbidity and mortality at medical centers throughout the world. In 2007, the Centers for Disease Control and Prevention (CDC) estimated the number of surgical site infections from inpatient surgery in U.S. hospitals to be approximately 300,000 cases, with the overall annual direct medical costs of HAI to U.S. hospitals estimated at approximately $30 billion.

In modern operating rooms, large overhead lightheads are commonly used to illuminate the surgical site. These lightheads are typically suspended from the ceiling, walls, or in some instances attached to mobile floor stands. The lightheads themselves typically have a large forward-facing region wherein illumination from the light sources exit through a window.

Many surgical lightheads incorporate an adjustment handle that may be located in the center of the aforementioned window. This handle provides the surgeon or surgical assistant the ability to position the overhead lamp and aim it at the region of interest of a patient. To avoid unnecessary confusion and to save time, the surgeon may manipulate the surgical lamp on his/her own. This handle is typically the only region of surgical lightheads that is considered sterile, as it is always covered by a disposable protective cover during surgery. Some medical centers use non-OEM handle covers purchased from third parties to reduce cost. These third-party cover systems typically require an adapter, provided by the handle cover vendor, to be mounted to the surgical lighthead to accept the cover.

During many surgical procedures, open surgical sites (wounds) present the opportunity for biological, and potentially biohazardous, matter to exit the patient and contaminate nearby equipment in the operating room. Similarly, a patient with an open surgical site is at risk to receive potentially biohazardous matter that has contaminated equipment during previous surgical procedures. Certain surgical procedures require the use of powered, high-impulse surgical instruments that are particularly efficient at atomizing or otherwise imparting a large amount of kinetic energy into biological materials. In these cases, biological contaminants can easily reach and adhere to the exposed, typically unsterile surfaces of surgical lightheads. These previously applied contaminants can later fall from the equipment into the open surgical sites of other patients. The resulting infection of the receiving patient can be deadly.

As mentioned previously, the window region of surgical lightheads can be very large in area and is also the face that is directed at the surgical site. Thus, this forward-facing region of the lighthead is prone to contamination by biological materials ejected from the surgical site. Surgical lightheads are also one of the few pieces of equipment that can be positioned directly over the surgical sites of patients, thus they are particularly at risk for shedding biohazardous contaminants into open wounds or contaminating autologous material ejected from a patient that may drop back into the open wound, and therefore present a high infection risk to patients.

Additionally, the large forward-facing region of the lighthead is a prime target for the surgeon, or any of the surgical staff, to inadvertently contaminate their gloves or other garments during a surgical procedure. This contamination could occur when reaching for the lighthead handle(s), maneuvering the lighthead, or even by unknowingly brushing past the lighthead. If the surgical staff member isn't aware they've become contaminated, the patient's risk for infection can increase dramatically.

Surprisingly, the forward-facing, light-emitting region of surgical lightheads is not typically covered or protected from contamination. Although these surfaces, depending on a medical center's specific cleaning protocol, may occasionally be wiped-down by surgical technicians, they are never considered sterile and are commonly left contaminated between patients. To date, the only region of surgical lightheads that are typically protected from contamination are the handle(s) used by the surgical staff to maneuver the physical position and/or control certain functions of the light.

Thus, what is needed is a disposable, temporary, sterile barrier or shield to protect the light-emitting or forward facing region of surgical lightheads. Replacing this shield (including, but not limited to between surgical procedures) would minimize the opportunity for surgical lightheads to transmit potentially biohazardous contaminants between patients, thus improving their clinical outcomes.

SUMMARY

An infection mitigation device providing a temporary, disposable sterile barrier between a sterile field and the non-sterile, light-emitting region of surgical lightheads is disclosed. The protective barrier can be easily applied and removed from the lighthead between each surgical procedure. The device minimizes the opportunity for biohazardous materials from being transmitted between patients, thereby reducing the chance of infection, and ultimately providing patients with improved clinical outcomes.

The barrier device can be configured to properly fit all lighthead models from all manufacturers. While many manufacturers produce round lightheads, this barrier device can be adapted to fit any shape lighthead, including, but not limited to square, rectangular, hexagonal, and oval. The device can be configured to partially or completely cover the forward-facing, light emitting region of the lighthead, as well extending well beyond that region to provide coverage for the sides and any non-sterile peripheral surfaces.

The barrier device can be composed of one or more types of translucent or transparent film. Depending on the attachment and manufacturing methods used, adhesives may be used to assemble and/or attach the film to the lighthead.

The surgical lightheads can be configured with a positioning and/or control handle located in the center region of the window where light is emitted. This handle can provide the surgeon, or surgical assistant, the ability to position the overhead lamp and aim it at the region of interest of a patient, as well as sometimes providing access to other controls, such as brightness and focus. This handle can be sterile, and can be covered by a disposable cover during surgery. The protective barrier device disclosed herein can be adapted to also receive and/or cover (partially or completely) one or more types of centrally located surgical lighthead adjustment handles. Where the existing central handle is configured with a camera, the barrier device can be adapted to cover those exposed surfaces as well, either at the manufacturer or at the location of use.

While the barrier can be adhered to the lighthead with conventional adhesives, a static cling effect can also be utilized. The barrier can also be attached via mechanical fixation, wherein the center handle and/or outer edge of the lighthead provide means to secure the device. Configuring the barrier such that the shape can provide integral geometric stability can allow for a much smaller region of attachment than a flat device. When the device is configured for attachment with adhesives, those adhesives may be selectively exposed or placed, as opposed to covering the entire surface. For example, installation and/or handling difficulty can be minimized by configuring the device to not have adhesives in the regions where the device is held. The adhesive locations can also be configured to only attach in specific regions, as opposed to large areas, thereby improving ease of installation.

Some medical centers use non-OEM handle covers purchased from third parties to reduce cost. These third-party cover systems typically require an adapter to be mounted to the surgical lighthead to accept the cover. The protective barrier device disclosed herein can be adapted to accommodate and/or mount to said adapters.

The device can be manufactured with a unitary or composite construction. For instance, one or more methods of integrated reinforcement can be utilized to provide geometric stability while the barrier is being positioned onto the lighthead. This could include laminating two or more layers of formed or non-formed material together or by integrating various combinations of dissimilar materials, such as metals, plastics, ceramics, fibers, fabrics, or combinations thereof.

A supportive carrier device may provide additional geometric stability for the barrier while it is maneuvered into its functional location on the lighthead. The carrier may be independent or separable from the barrier device.

The device may also be configured as a laminated group of multiple disposable layers. The laminated group can be applied to the lighthead and then the exposed layer can be removed and disposed of as needed (including, but not limited to between surgical procedures).

BRIEF DESCRIPTION OF THE DRAWINGS

FIG. 3b is a close-up view of a variation of FIG. 3a.

FIG. 5 is a perspective view of a variation of the sterile barrier having an integrated handle cover.

FIG. 6a is a perspective view of a variation of the sterile barrier having an integrated camera handle cover with a control interface region.

FIG. 6b is a close-up view of a variation of FIG. 6a.

FIGS. 7a and 7b are exploded perspective and side views, respectively, of a variation of a cone shaped sterile barrier configured for retrofitting a camera cover.

FIG. 7a' is a close-up view of a variation of FIG. 7a.

FIG. 7c is a perspective view of a variation of a cone shaped sterile barrier with an accordion center configured for retrofitting a camera cover.

FIG. 7c' is a close-up view of a variation of cross-section A-A of FIG. 7c.

FIGS. 8a and 8b are exploded perspective and side views, respectively, of a variation of a cone shaped sterile barrier configured for retrofitting a rigid handle.

FIG. 11a is a perspective view of a variation of a sterile barrier with a wire reinforcement.

FIG. 11a' is a close-up view of a variation of FIG. 11b.

FIG. 11b' is a close-up view of a variation of FIG. 11b.

REFERENCE NUMERALS

001: Surgical Lighthead Assembly
002: Surgical Lighthead Window
003: Standard Handle for Surgical Lighthead
004: Camera Handle for Surgical Lighthead
005: Disposable Sterile Cover for Standard Handle
006: Disposable Sterile Cover for Camera Handle
007: Retrofit Adapter for Standard Handle—Rigid
008: Retrofit Adapter for Standard Handle—Flexible
009: Retrofit Adapter for Camera Handle
010: Disposable Rigid Retrofit Handle
011: Disposable Flexible Sterile Cover for Retrofit Handle Adapter
012: Disposable Rigid Retrofit Camera Sterile Cover
013: Surgical Lighthead Support Arm
014: Surgical Lighthead Auxiliary Handle
015: Surgical Lighthead Window—No Handle
100: Sterile Barrier—Feathered Center
105: Sterile Barrier—Circular Center
110: Sterile Barrier—Accordion Center 115: Sterile Barrier—Integrated Handle Cover
120: Sterile Barrier—Integrated Camera Handle Cover with Control Interface Region
125: Sterile Barrier—Retrofit Camera Handle
130: Sterile Barrier—Retrofit Rigid Handle
135: Sterile Barrier—Retrofit Flexible Handle
140: Sterile Barrier—Accordion—Retrofit Camera Handle
141: Sterile Barrier—No Hole—Conically Shaped
142: Sterile Barrier—No Hole—Flat
143: Sterile Barrier—Wire Reinforced
145: Exposed Adhesive Location
150: Peel Tab
155: Wire Reinforcement
160: Flat Reinforcement
165: Formed Reinforcement Layer
170: Reinforcement Rib
175: Accordion Convolutions
180: Feathered Edge
185: Lighthead Control Interface Region
190: Overlapping Laminated Edge
195: Integrated Camera Handle Cover
200: Multi-Layer Sterile Barrier System
205a: Peelable Layer of Multi-Layer Sterile Barrier System
205b: Peelable Layer of Multi-Layer Sterile Barrier System
205c: Peelable Layer of Multi-Layer Sterile Barrier System
205d: Peelable Layer of Multi-Layer Sterile Barrier System
300: Installation Support Carrier
400: Arrow—Peeling Sterile Barrier to Separate from Lighthead
405: Arrow—Removing Sterile Barrier for Disposal
410: Arrow—Sterile Barrier Installation

DESCRIPTION

Figure 1:
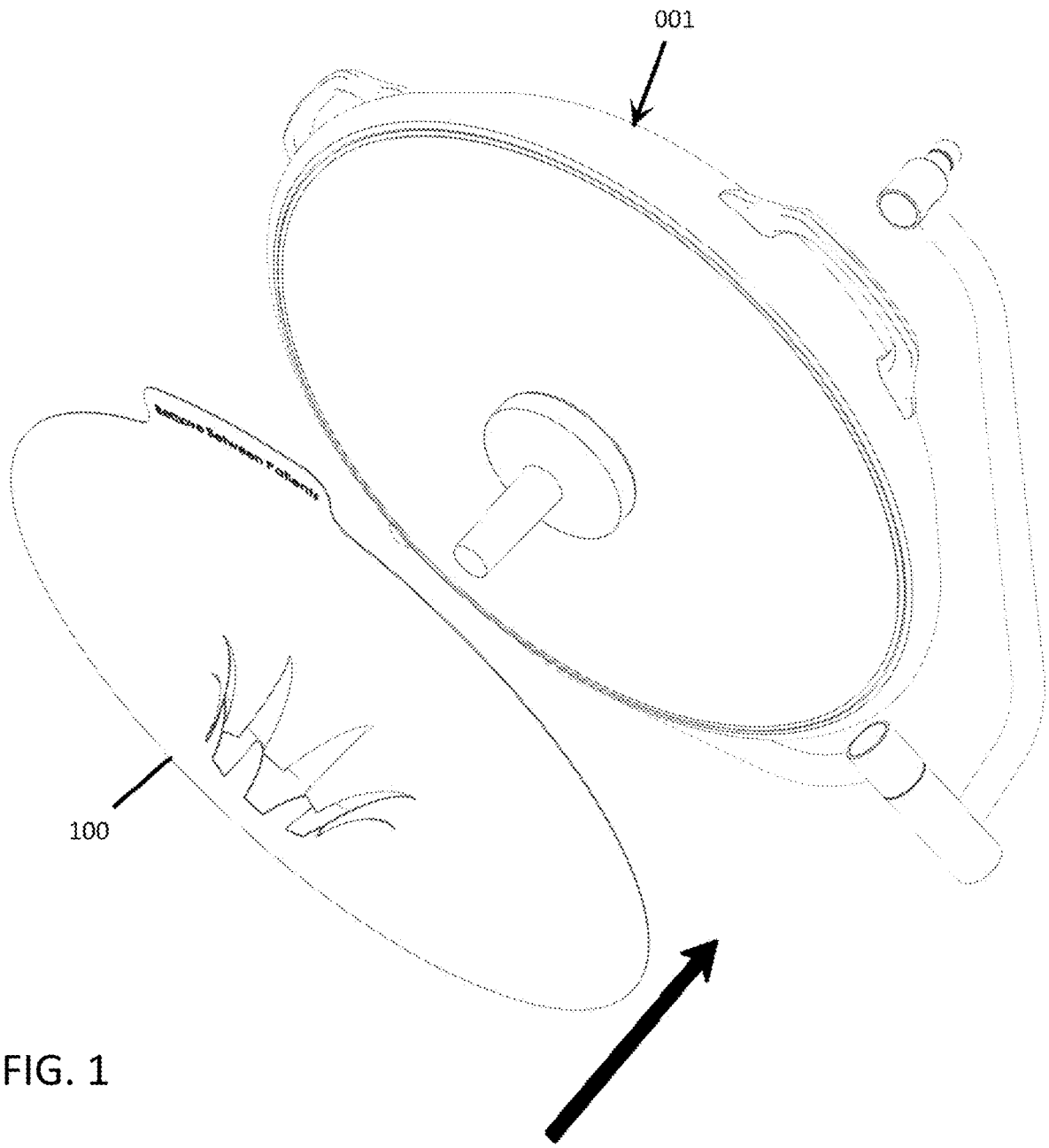
FIG. 1 is a perspective view of a variation of a method for applying the sterile barrier with a feathered center to a surgical lighthead.

FIG. 1 illustrates that, a sterile protective barrier device 100 (also referred to herein as a barrier) can be attached, as shown by arrow, to a generic surgical lighthead assembly 001 (also referred to herein as a surgical lighthead). The Surgical lighthead assembly can have a light source and a light emission window 002 through which light from the light source passes when the light source is emitting light. Light emission windows can be round in shape, but can also be rectangular, square, triangular, hexagonal, oval, or any combination thereof. The sterile protective barrier device (e.g. 100) can be configured to match, or extend past, the perimeter, periphery, circumference, or outer diameter of the light emission window and/or surgical lighthead assembly.

Figure 2:
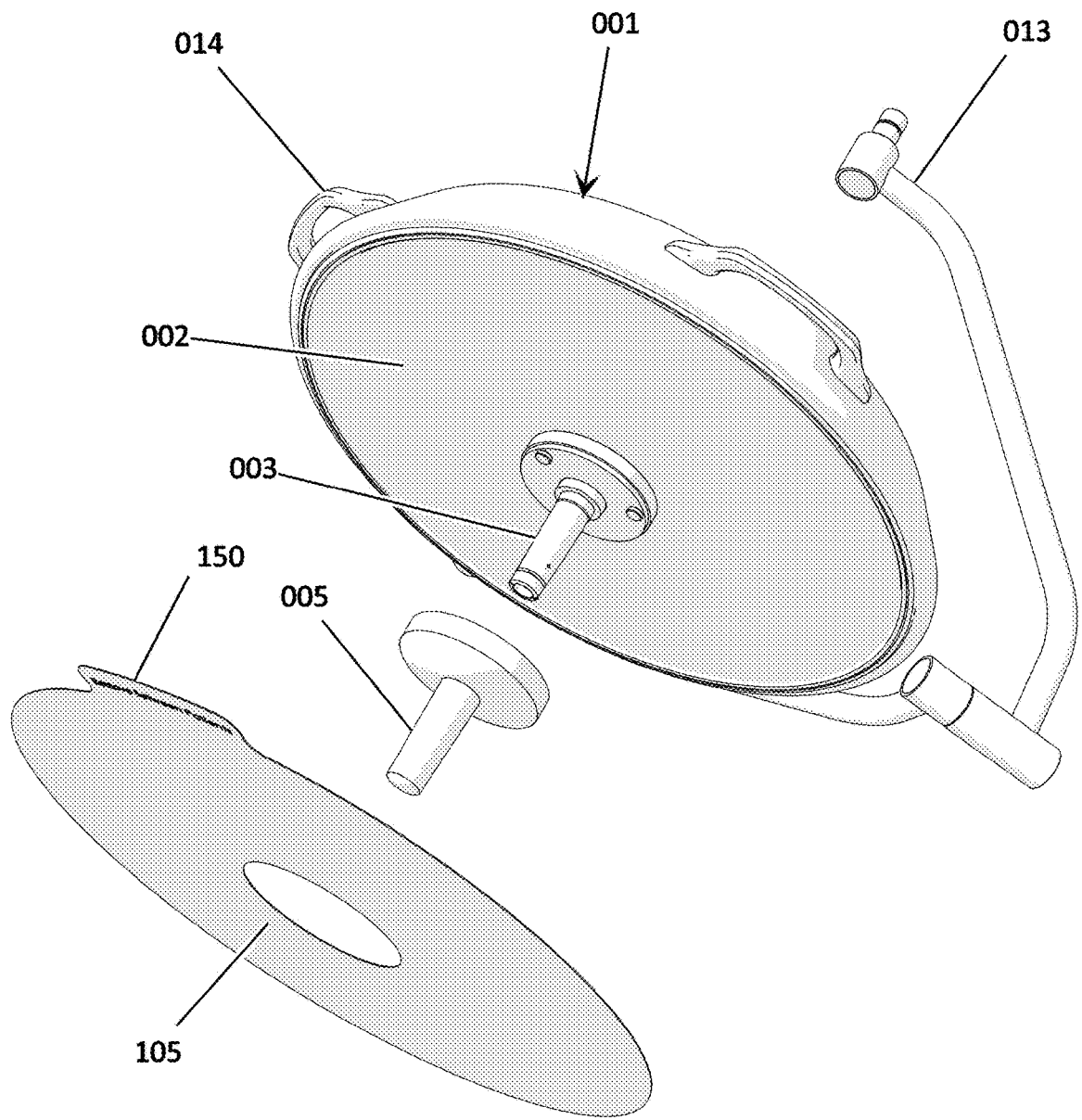
FIG. 2 is a perspective exploded view of a variation of the sterile barrier with a circular center, disposable handle cover, and a lighthead with standard handle.
Figure 4:
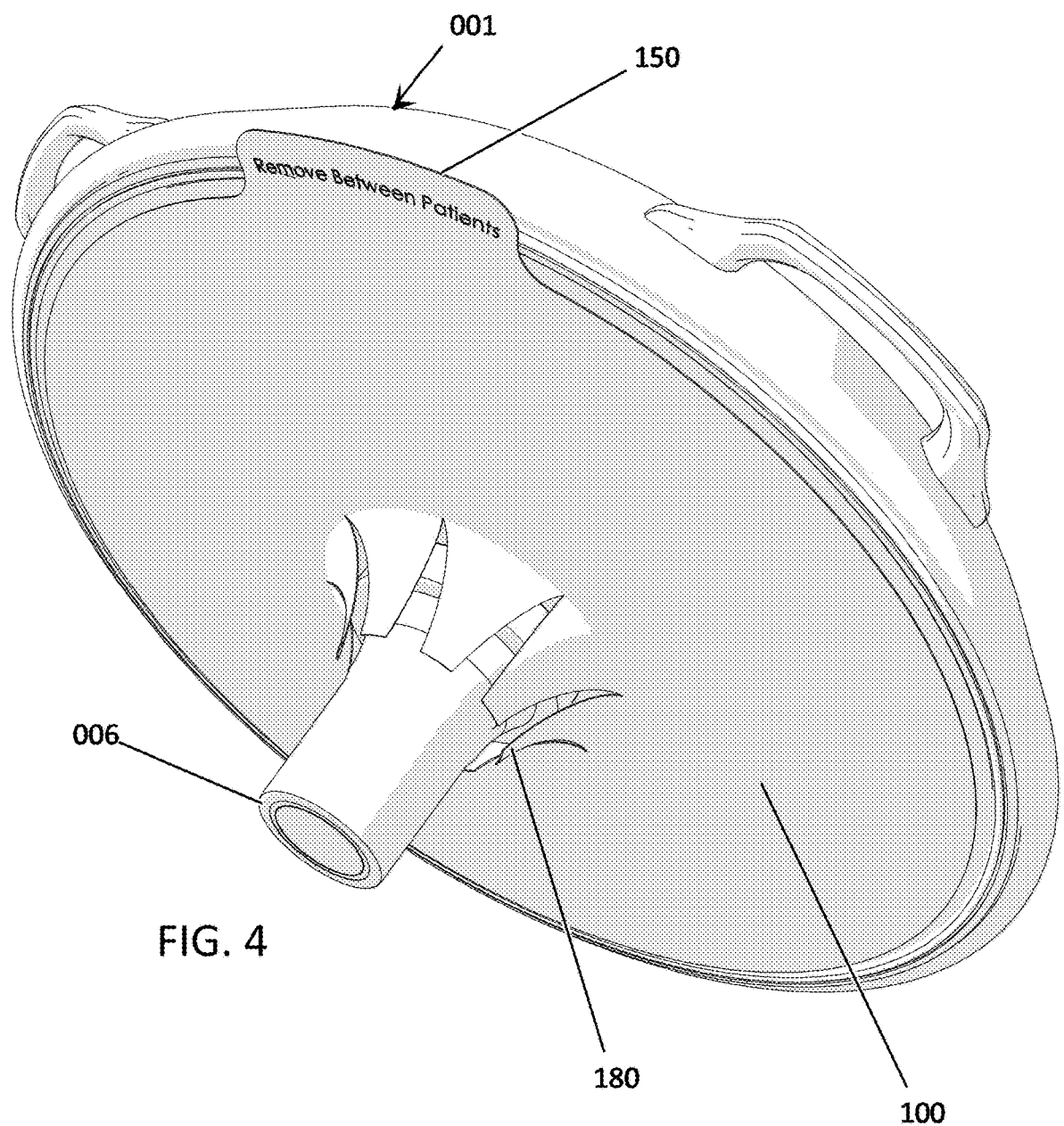
FIG. 4 is a perspective view of a variation of the sterile barrier with a feathered center applied to the surgical lighthead with a camera handle.
Figure 10:
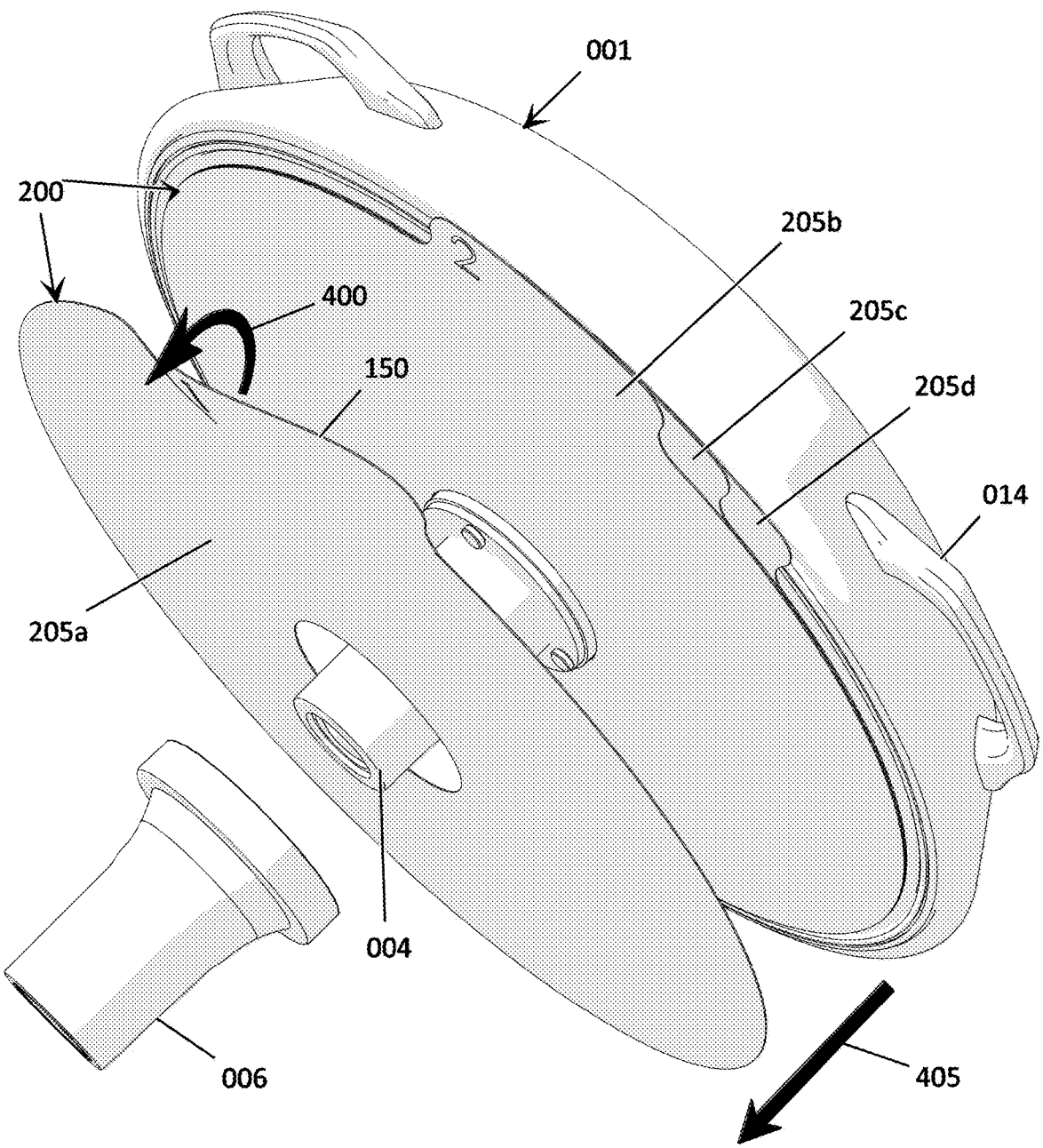
FIG. 10 is an exploded perspective view of a variation of a multi-layer peelable cover system.

Referring to FIG. 2, surgical lightheads can be ceiling-mounted with a support arm 013, or also mounted to mobile floor-stands, walls, or other equipment within proximity of the lighthead. Surgical lightheads can have standard handles 003 extending out from the light emission window 002. Standard handles can be centrally located on and extend perpendicularly from the light emission window 002. The standard handles 003 can be completely or partially covered by a disposable sterile handle cover 005. One or more cameras 004 can extend through the standard handle 003, as illustrated in FIGS. 7a and 10. The cameras 004 can also be covered with a disposable sterile cover 006, as shown in FIGS. 4 and 10. As illustrated in FIG. 2, the surgical lightheads can have auxiliary handles 014 that can extend radially from the surgical lighthead assembly 001. The sterile protective barrier device can have one or more peel tabs 150. The sterile protective barrier can be manufactured from one or more of many commercially available techniques, such as thermoforming, die-cutting, adhesives, and/or thermal-fusion.

Center Variations

Figure 3A:
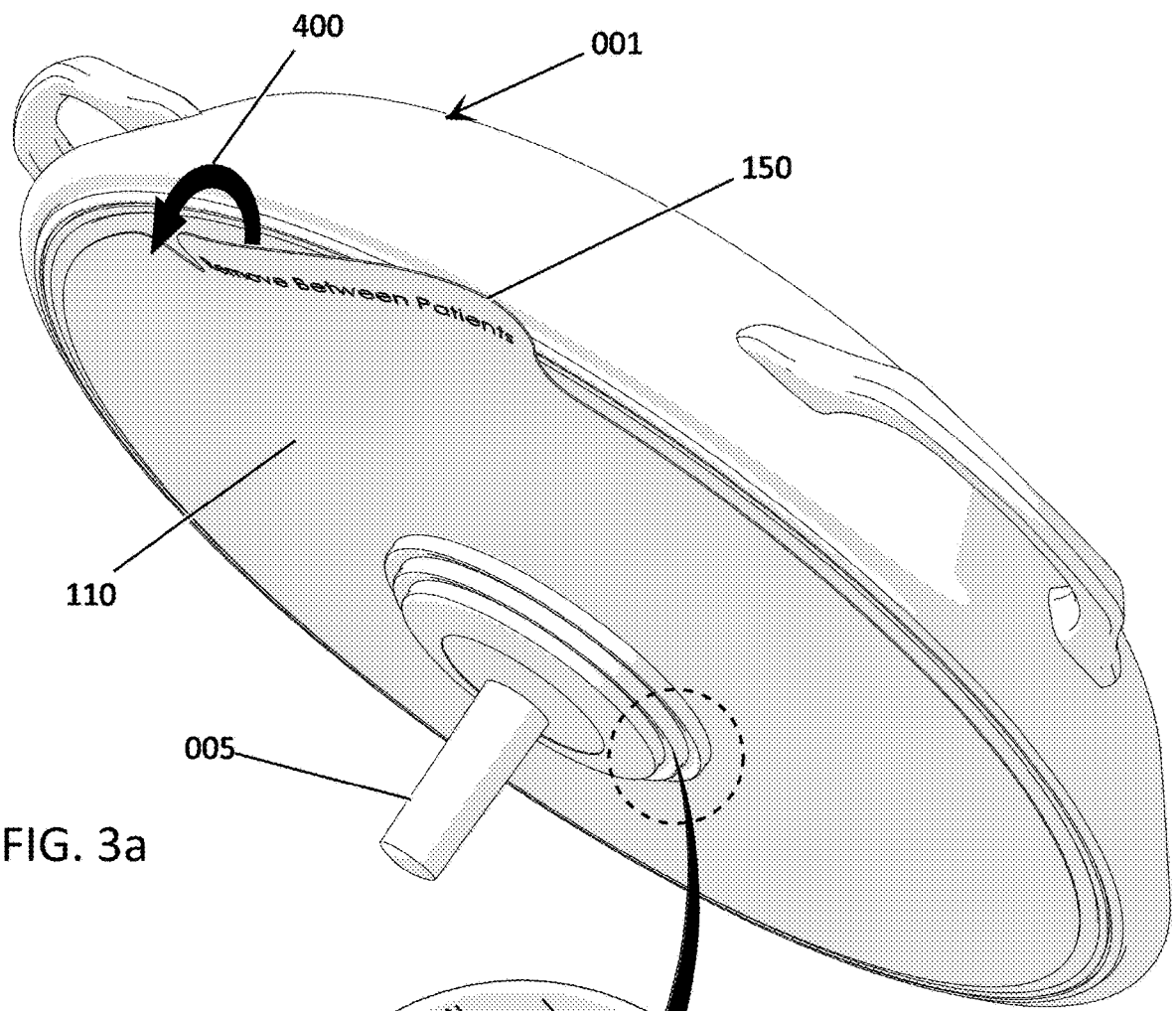
FIG. 3a is a perspective view of a variation of a method of removing the sterile barrier with an accordion center from the lighthead with a disposable handle cover.
Figure 3B:
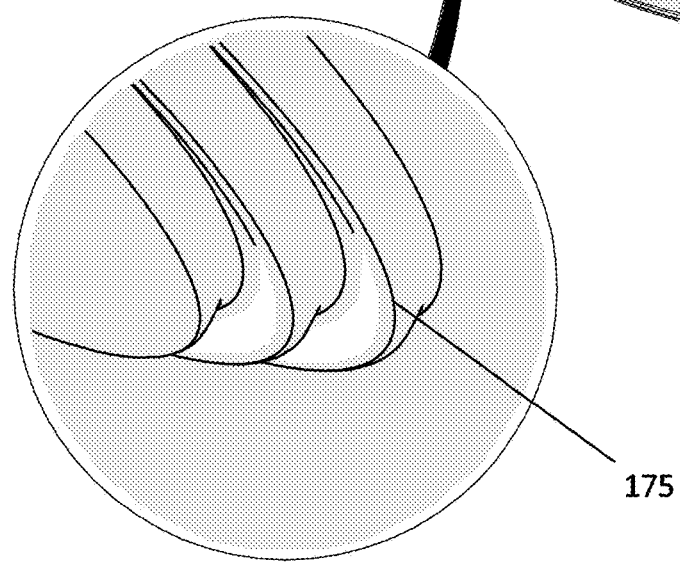
Figure 14A:
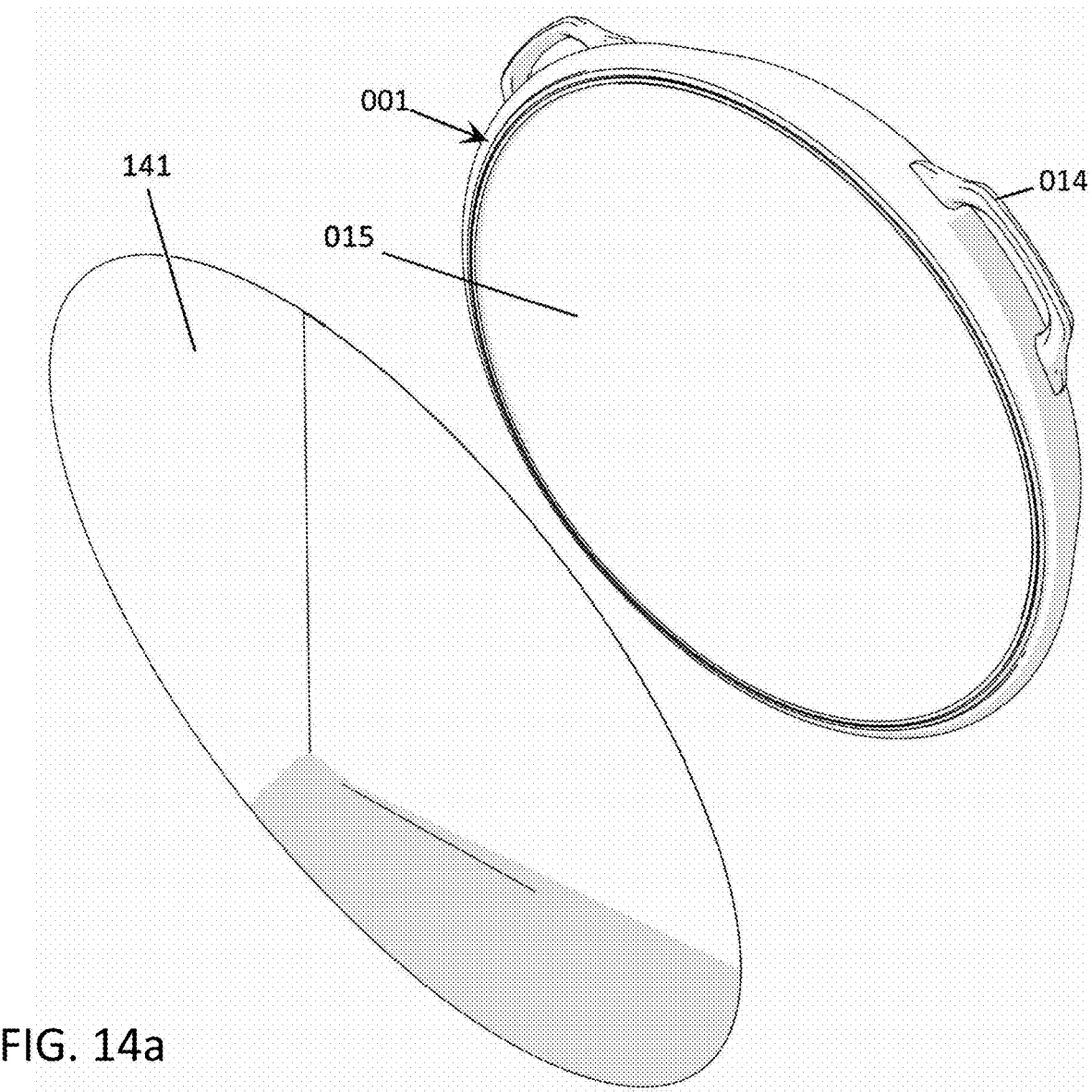
FIG. 14a is a perspective view of a variation of a conically shaped sterile barrier with no hole and no handle located on the light emission window of the lighthead.
Figure 14B:
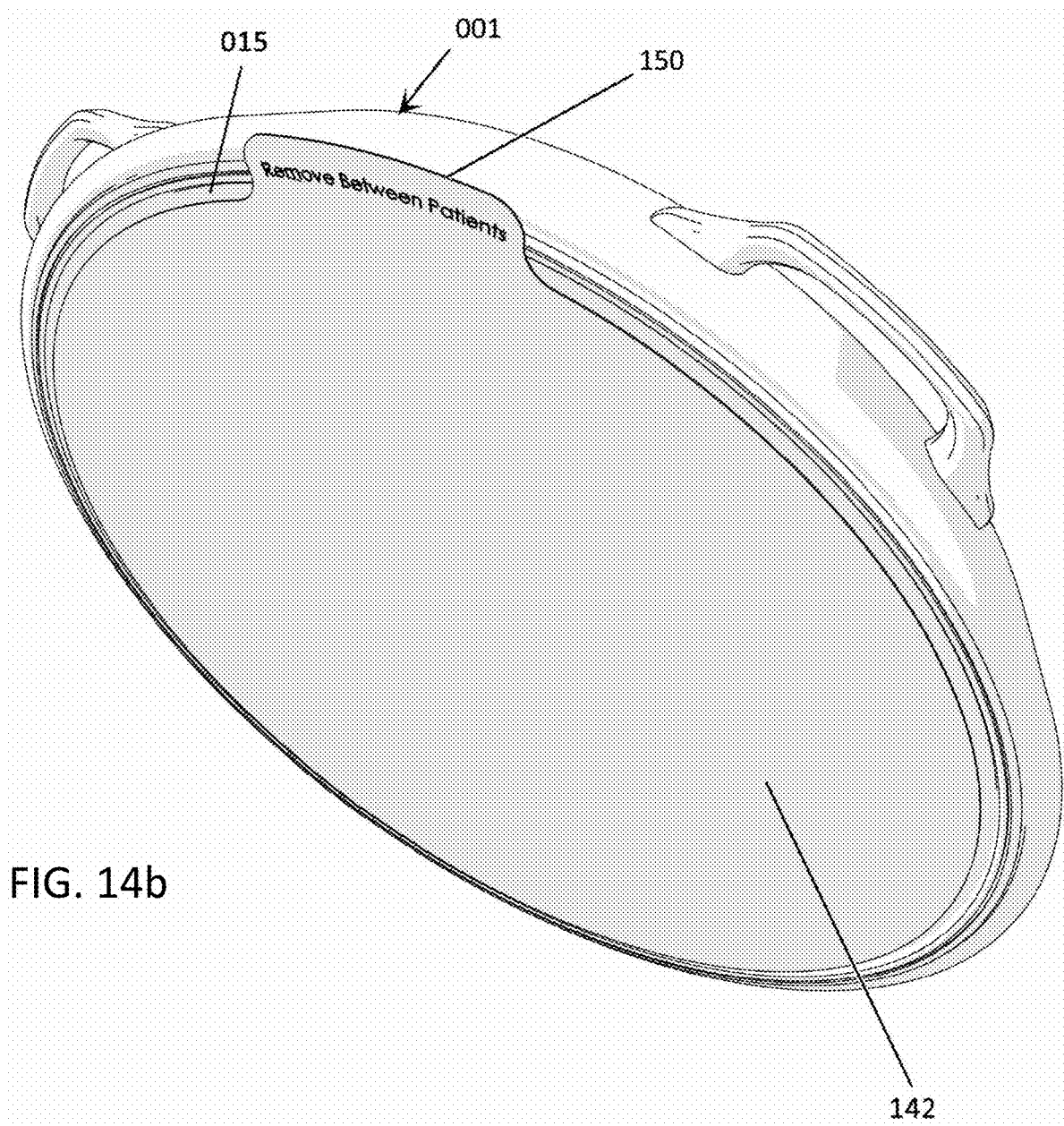
FIG. 14b is a perspective view of a variation of a flat shaped sterile barrier with no hole and no handle located on the light emission window of the lighthead.

The sterile protective barrier (e.g. 100-140, 200) can cover standard handles 003 and/or camera handles 004. FIG. 2 discloses a sterile barrier 105 with a circular center. FIG. 3 discloses a sterile barrier 110 with an articulating accordion center 175. FIG. 4 discloses a feathered center sterile barrier 100 with a feathered edge 180. FIG. 5 discloses a sterile barrier 115 with an integrated handle cover. FIG. 6 discloses a sterile barrier 120 with an integrated camera handle cover 195, wherein the cover may be configured with a control access region 185. The aforementioned features can be manufactured from one or more of many commercially available techniques, including, but not limited to vacuum forming, die-cutting, adhesives, and/or thermal-fusion. For instance, the handle/camera cover geometry can be thermoformed as an integral feature to the sterile barrier device, or it can be manufactured separately and subsequently adhered/fused together. FIGS. 14a and 14b disclose surgical lightheads with no standard handle located on the light emission window 015. FIG. 14a discloses a conically shaped barrier variation 141 and FIG. 14b discloses a flat barrier variation 142. Variations 141 and 142 that don't have a hole can be attached to the lighthead 001 via adhesives, fasteners, and/or clamps.

Retrofit Kit Compatability

Figure 9A:
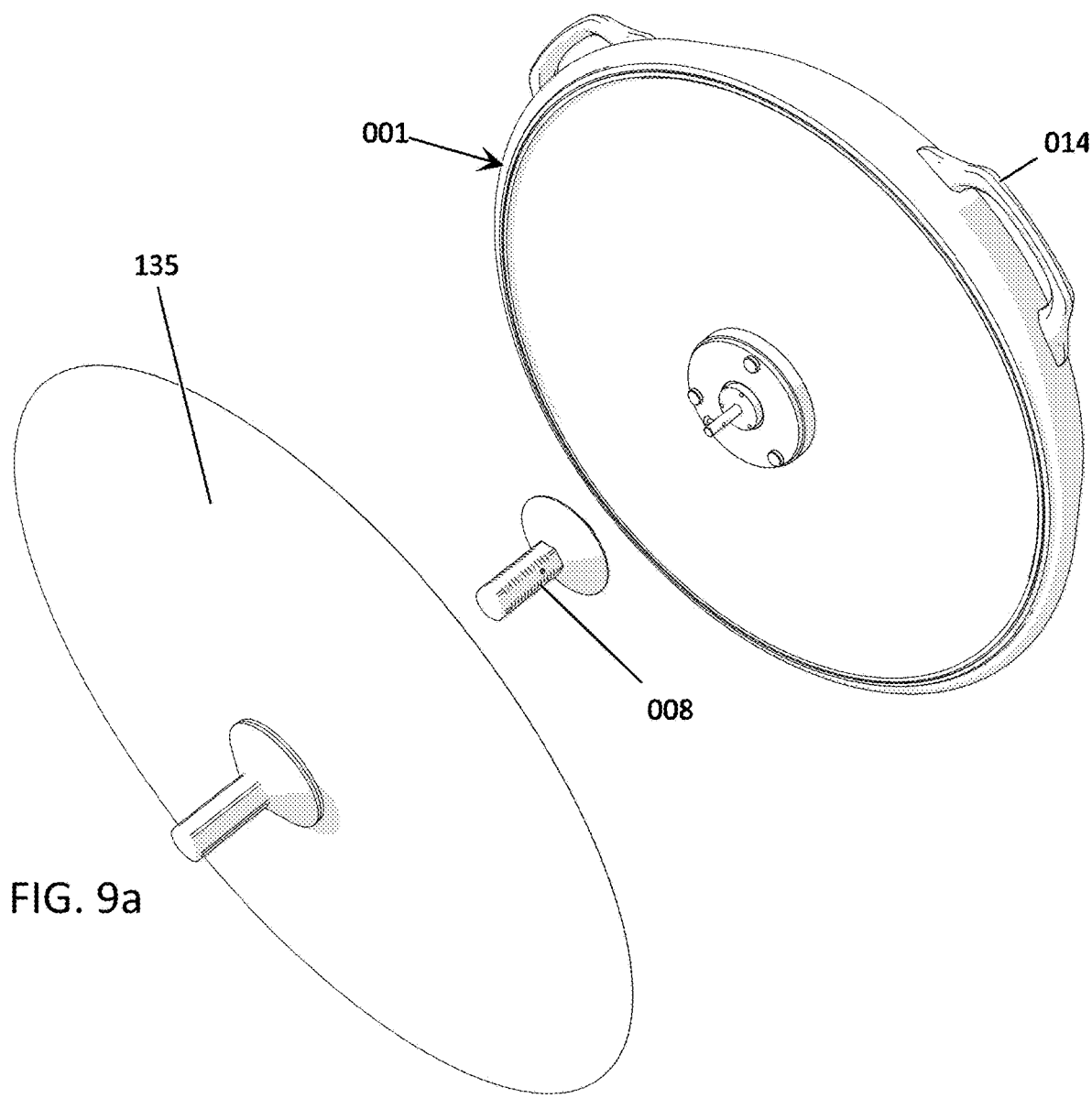
FIGS. 9a and 9b are exploded perspective and side views, respectively, of a variation of a cone shaped sterile barrier configured for retrofitting a flexible handle cover.

Surgical lightheads 001 can be configured with aftermarket, non-OEM retrofit handle cover systems as illustrated in FIGS. 7a, 8a, and 9a. These third-party cover systems typically require an adapter (e.g. 009, 007, or 008 respectively), to be mounted to the surgical lighthead to accept a standardized disposable cover (e.g. 005, 006, 011, or 012) or disposable handle (e.g. 010). The protective barrier device disclosed herein can be adapted to accommodate and/or mount to said adapters. FIG. 7a discloses a disposable barrier 125 configured to be compatible with camera handle 004 retrofit adapters 009 and disposable camera covers 012. The retrofit system (e.g. 007, 008, 009, 010, and 012) illustrated in FIGS. 9a and 9b can have a thin, flexible disposable handle cover 011 (not shown) and a flexible retrofit handle adapter 008. The barrier (e.g. 125, 130, 135, or 140) can be conical or partially conical in form. The disposable handle cover 011 can be slid onto flexible retrofit handle adapter 008. The sterile barrier 135 incorporates a flexible handle cover that extends radially beyond the handle 008 to also create a sterile barrier for the surgical lighthead window 002. The disposable barrier 135 and its variants can be manufactured from one or more of many commercially available techniques, such as thermoforming, die-cutting, adhesives, and/or thermal-fusion. FIGS. 7a' and 7b illustrate the overlapped edges 190 of a disposable barrier 125 manufactured by die-cutting can be subsequently adhered (i.e., the two open edges) together to create a self-supporting form.

Figure 9B:
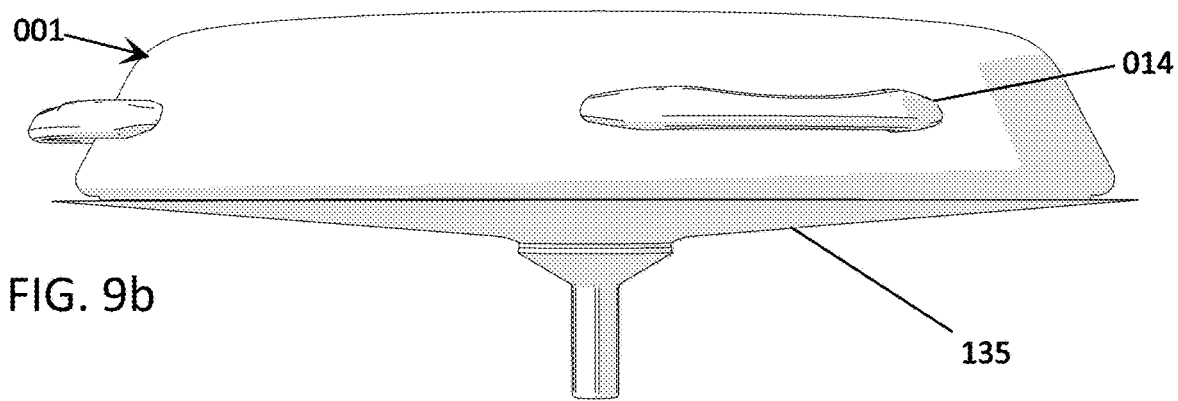

FIGS. 7c and 7c' disclose a disposable barrier 140 with articulating coaxial accordion ripples, corrugations, or convolutions 175. FIGS. 8a and 8b disclose a disposable barrier 130 configured to be compatible with a disposable rigid retrofit handle 010 and retrofit adapter 007. Similar to the barrier devices 125 and 140 disclosed above for retrofit camera covers, the barrier 130 can be retained by the disposable handle. Also similar to barrier 125, barrier 130 can have accordion ripples, corrugations, or convolutions 175. FIGS. 9a and 9b disclose a disposable barrier 135 configured to be compatible with a disposable flexible retrofit handle adapter 008. Similar to the barrier devices 125 and 130 disclosed above, the barrier 135 can be retained (i.e., held to the surgical lighthead) by the retrofit adapter 008, and can also be configured with accordion convolutions 175.

Multi-Layer Peelable Barrier

FIG. 10 discloses a multi-layer, laminated sterile barrier system 200, containing a plurality of peelable layers 205a, 205b, 205c, and 205d.

Barrier Reinforcement

Figure 11B:
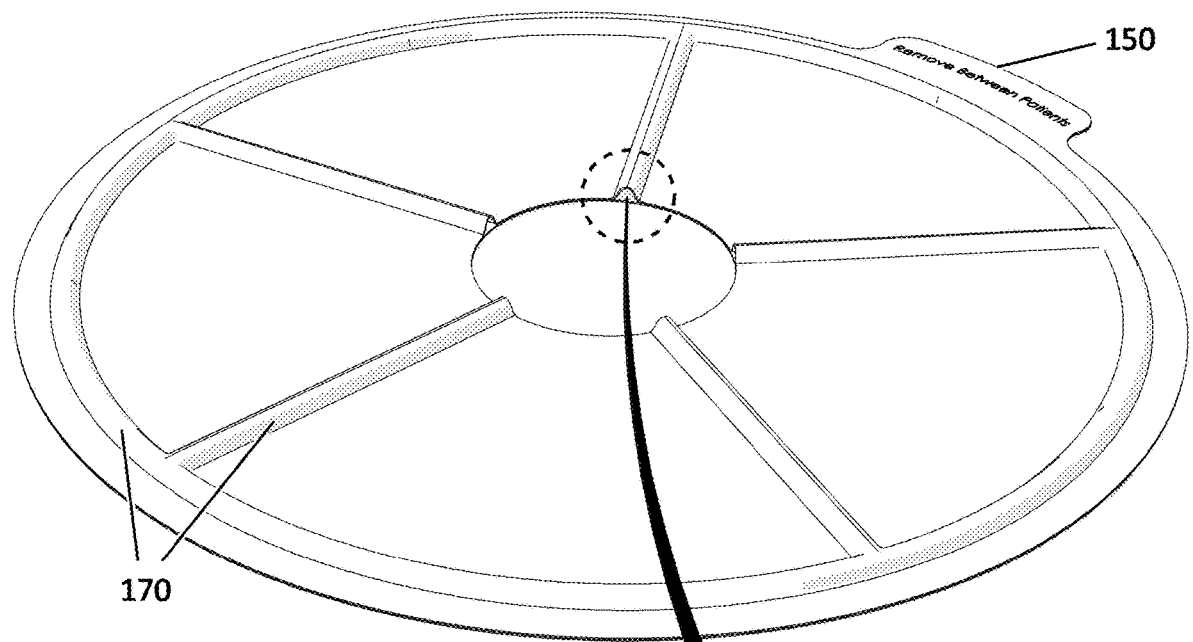
FIG. 11b is a perspective view of a variation of a sterile barrier with a formed plastic film reinforcement.
Figure 11B:
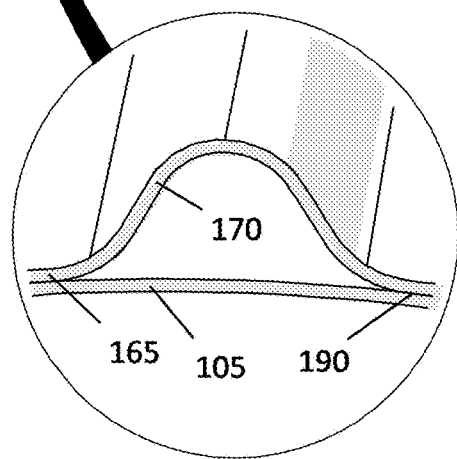
Figure 11C:
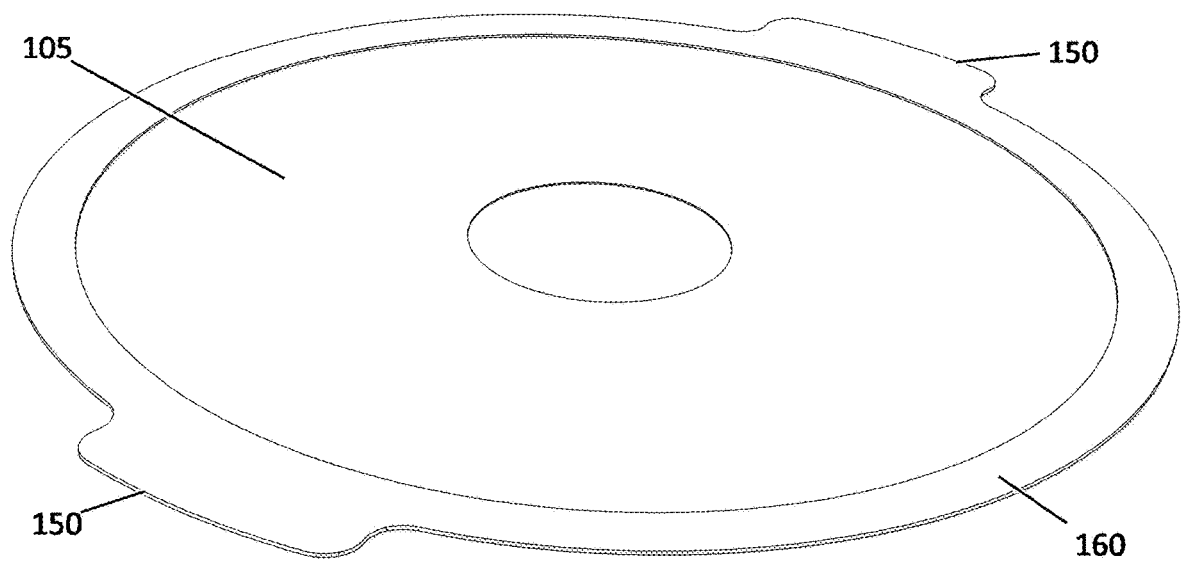
FIG. 11c is a perspective view of a variation of the sterile barrier with a flat plastic film reinforcement.

FIGS. 11a, 11a', 11b, 11b', and 11c disclose integrated reinforcement variations for the sterile barrier device. FIGS. 11a and 11a' disclose the implementation of wire reinforcement 155. These wire reinforcements could be formed, molded, and/or welded. In one variation, as disclosed in the detail view of FIG. 11a, the barrier 143 has an overlap 190 on the wire reinforcement 155 to retain the barrier 105. The wire reinforcement could also be directly attached with other methods including adhesive tape or thermal fusion. FIGS. 11b and 11b' discloses the implementation of a secondary layer of formed plastic film 165, with reinforcement ridges or features 170, laminated onto the primary barrier layer 143. Depending on various factors, such as material type and geometry, formed layer 165 may be adequately stabilized such that the separate barrier layer 143 is not required. Reinforcement features 170 may also be a plurality of smaller subcomponents that are attached to specific regions of the barrier layer 143. FIG. 11c discloses the implementation of flat reinforcement material 160 applied to the sterile barrier 105.

Installation Support Carrier

Figure 12:
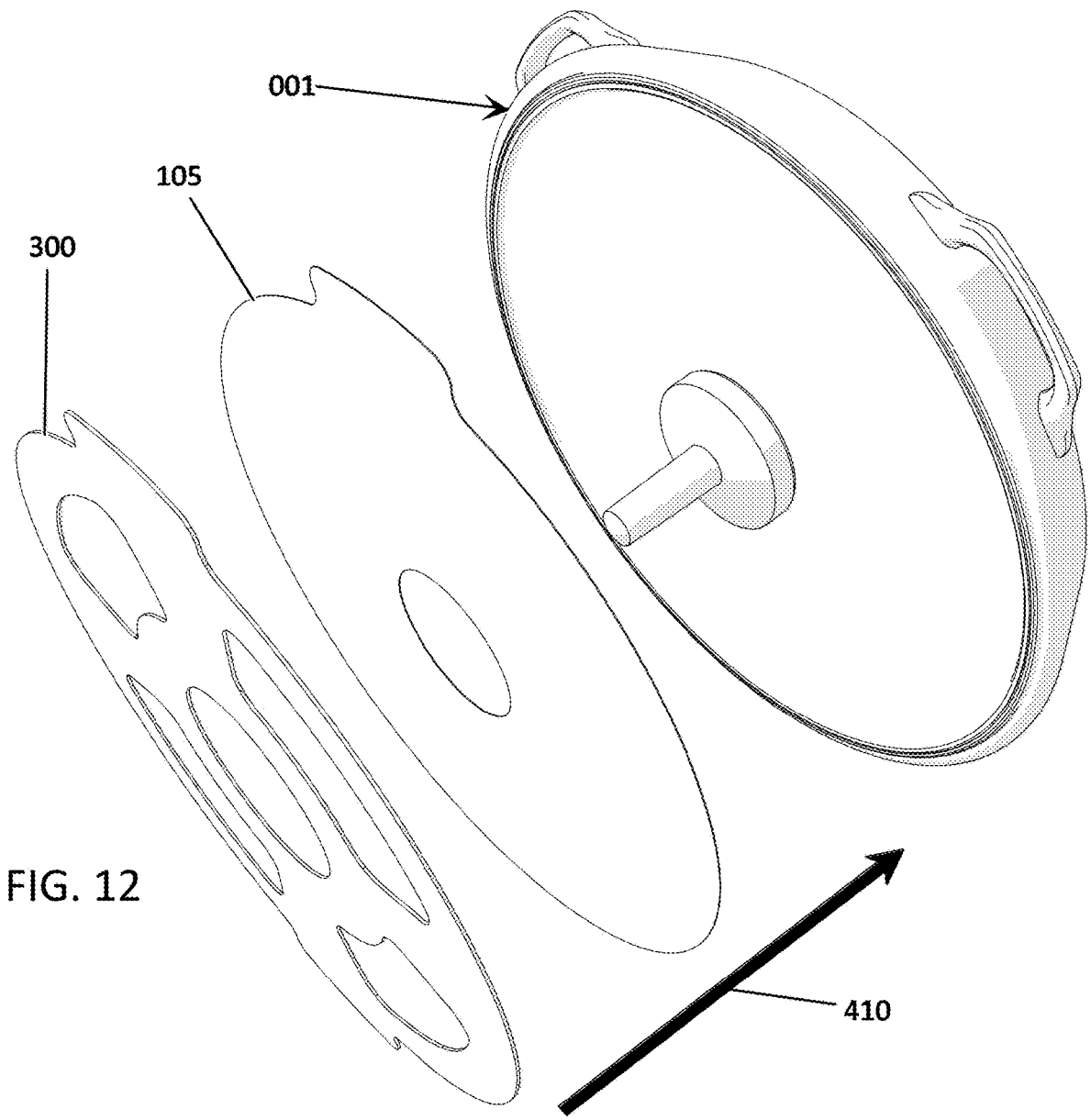
FIG. 12 is a perspective view of a variation of a method for using a sterile barrier with an installation support carrier.

FIG. 12 discloses a support device 300 that the sterile barrier 105 is carried or stabilized by until said barrier is attached to the surgical lighthead. This support device could be manufactured from a wide range of materials, transparent/translucent as well as opaque.

Adhesive Variations

Figure 13A:
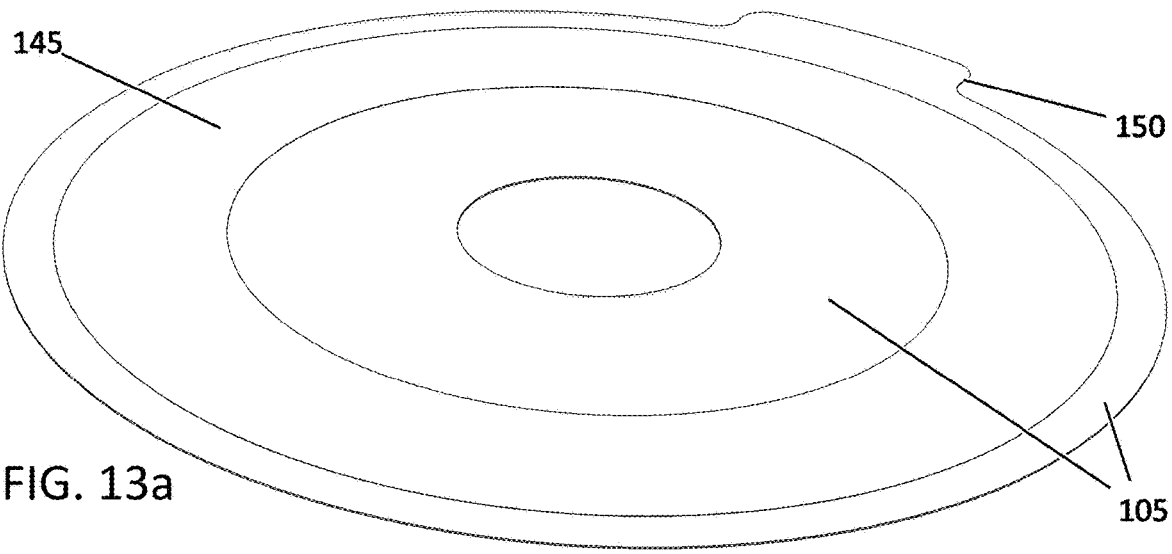
FIGS. 13a through 13e are perspective views of variations of the sterile barrier with exposed adhesive in different locations.
Figure 13B:
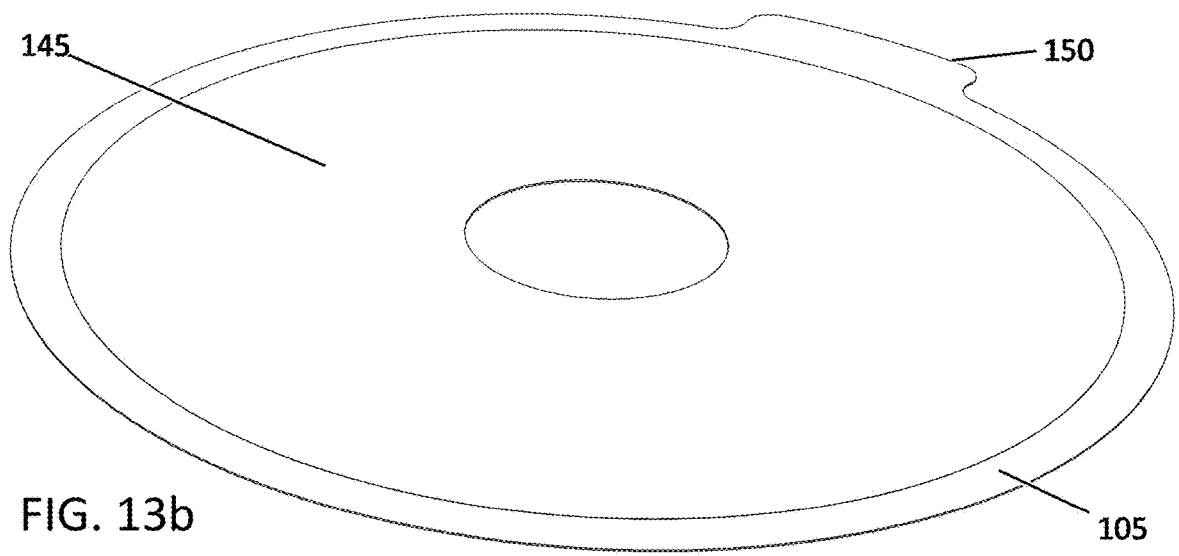
Figure 13C:
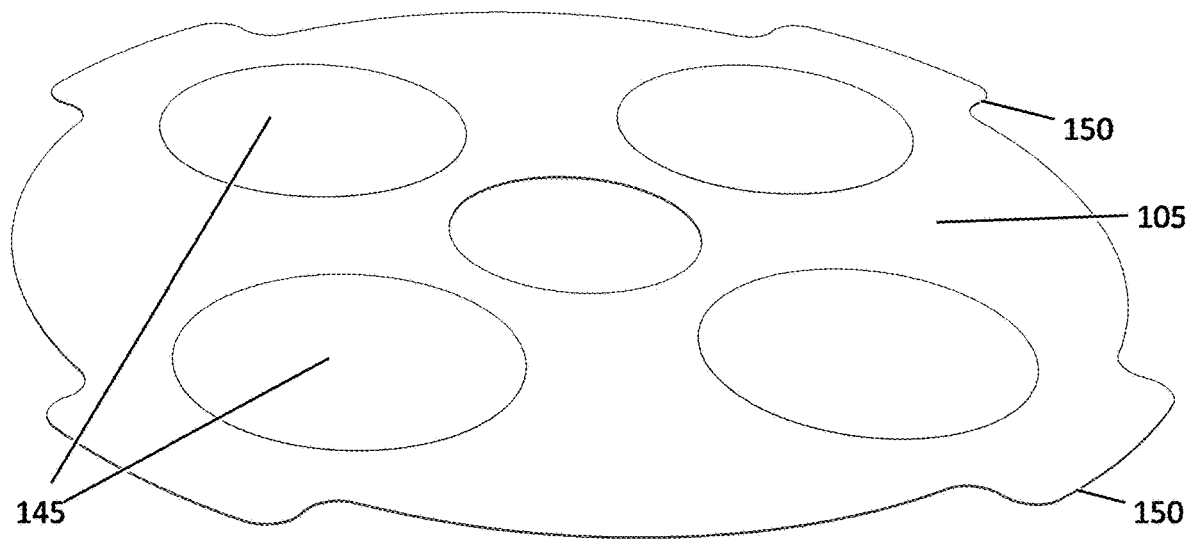
Figure 13D:
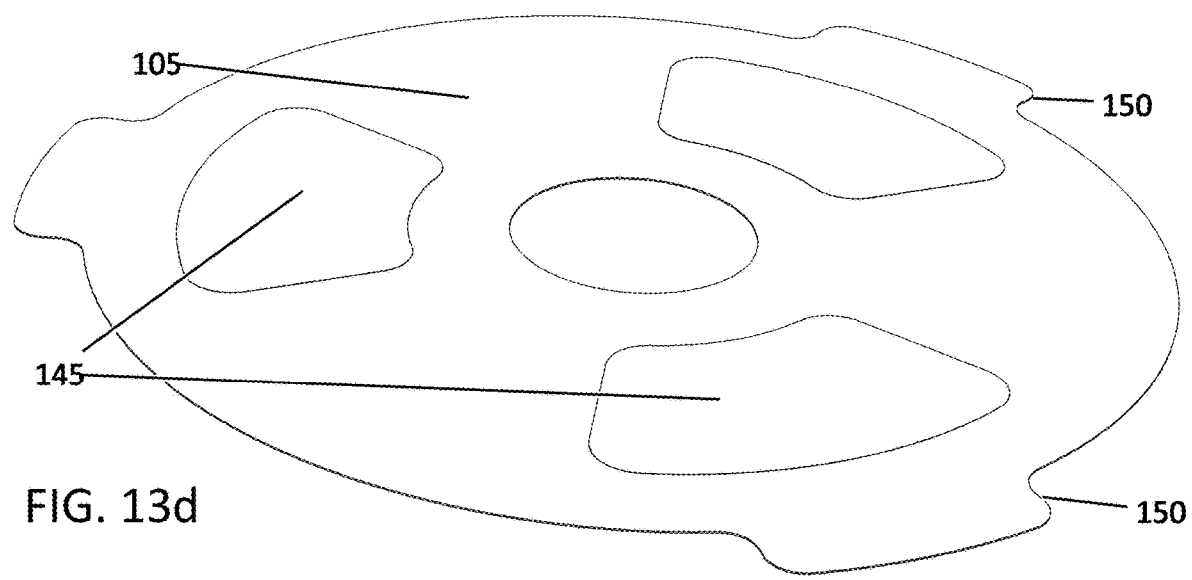
Figure 13E:
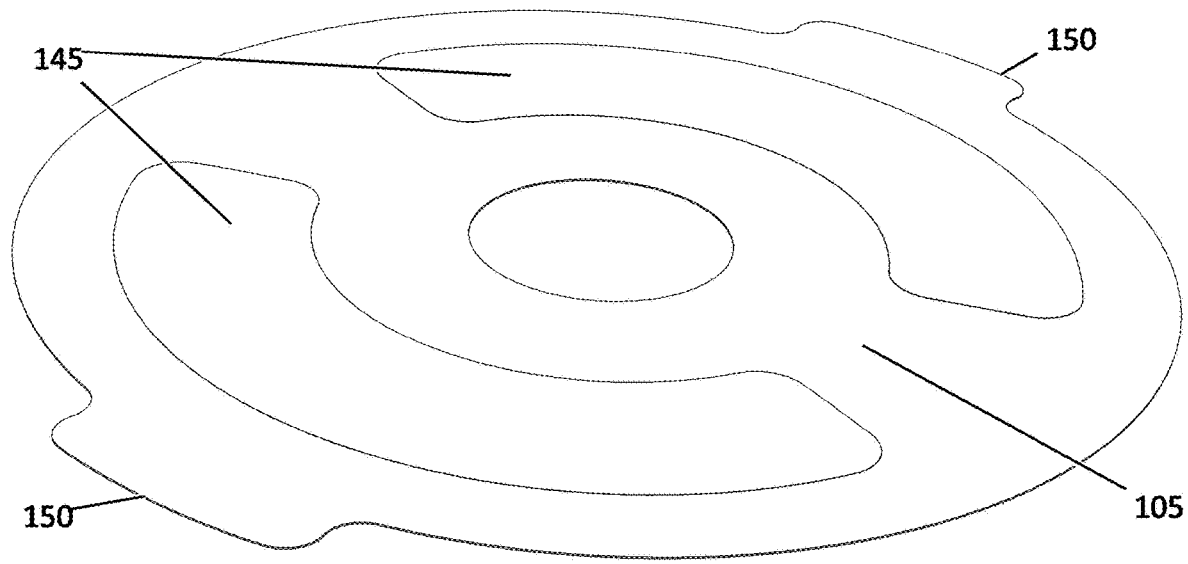

FIGS. 13a thru 13e disclose variations for applications requiring adhesives. The barrier 105 can have barrier film with exposed adhesive in location(s) 145. One or more peel tabs 150 can be placed in different orientations extending from the circumference of the barrier 105. For example, the barrier 105 can have a single peel tab 150 (as shown in FIGS. 13a and 13b), four peel tabs 150 spread at 90 degrees from each other, with two sets of diametrically opposed peel tabs 150 (as shown in FIG. 13c), three peel tabs 150 spread at 120 degrees from each other (as shown in FIG. 13d), two peel tabs diametrically opposed to each other (as shown in FIG. 13e), or overlapping combinations thereof. Adhesives may be applied to selected portions or the entire surface of the barrier film. The barrier 150 can then be laminated with another thin film that is configured to only expose adhesive locations 145 as required. Adhesive type and location selection can be based on several factors, including providing adequate adhesion, ease of installation and removal, and minimizing or eliminating any residue remaining on the surgical lighthead after removal. Certain regions (e.g. Peel Tab 150) of the disposable barrier 105 can be configured to be devoid of adhesives to minimize the chances for unwanted adhesion with the gloved hands of the user handling the device. Conventional adhesives, as well as a multitude of other attachment means, such as magnets, elastic bands, friction, Velcro, static cling, suction, mechanical fasteners, or a combination thereof can be attached to the barrier film at the locations 145. Non-flat or Conically shaped sterile barriers can use adhesives as a method of attachment.

Material Variations

The protective barrier device can be composed of one or more types of transparent or translucent material, including, but not limited to Polyethylene Terephthalate (PET), Polyester (PE), Polycarbonate (PC), Polymethyl Methacrylate (PMMA), Polystyrene (PS), Polyurethane (PUR and PU), Copolyester (PETG), Fluorinated Ethylene Propylene (FEP), Perfluoroalkoxy Polymer (PFA), Polytetrafluoroethylene (Teflon), Polychlorotrifluoroethene (PCTFE or PTFCE), Biaxially-oriented polyethylene terephthalate (Bo-PET), Biaxial Oriented Polyethylene Naphthalate (PEN), Cellulose Acetate (CA), Styrene Acrylonitrile (SAN), Polyphenylsulfone (PPSU), Polyetheretherketone (PEEK), Polyimide (PI), Polysulfone (PSU), or combinations thereof.

The protective barrier may pass or absorb specific wavelengths or bands of radiation within or outside the visual spectrum. Other non-translucent/transparent materials may be suitable for regions not requiring light-transmission. For example, the reinforcement materials could include metal alloys, fiber-reinforcement, composites, plastics, resins, paper products, and combinations thereof.

OPERATION

Disclosed in FIG. 1 is a sterile protective barrier device 100 being applied to the exposed, non-sterile surface of a surgical lighthead 001, for example, to protect against potentially biohazardous contamination. The sterile barrier device (e.g. 100) can be applied to the surgical lighthead 001 by one of the surgical staff prior to the surgical procedure, and then, for example as shown in FIG. 3, removed (as shown by arrow 400) by pulling the peel tab(s) 150 away from the surgical lighthead 001 and disposed of as needed. Referring to FIG. 2, illumination can be emitted from a window 002. This region is also one of the most at risk for contamination, as it is usually pointed in the direction of the surgical site. This window surface is also at risk for being inadvertently touched by the surgical staff, partially due to its proximity to the lighthead positioning handle 003. Surgical lightheads may have a camera 004 (FIG. 7a) in-place of a standard lighthead positioning handle 003. However, the camera may still be utilized to position and control the lighthead and/or camera functions. Some surgical lightheads may have auxiliary handles 014, but they are frequently not covered by sterile barriers, nor are they intentionally contacted during surgical procedures.

Center Variations

As illustrated in FIG. 2, surgical lightheads can have centrally located positioning/control handles 003. The handles 003 can have or be cameras, as illustrated in FIGS. 7a and 10. The handles can be used by the surgical staff and/or surgeons to position the surgical lighthead 001 and to access some or all controls for the light and/or camera 004 during surgical procedures as shown in FIG. 6. These non-sterile handles can be covered by disposable sterile covers 005 and/or 006 (FIGS. 2 and 10) to minimize the opportunity for biological contaminants to be transferred between patients.

The sterile protective barrier (e.g. 100) can be configured in a multitude of variations to adapt to or cover standard handles 003 and camera handles 004. FIG. 2 discloses a sterile barrier 105 with a round cutout center. FIG. 3 discloses a sterile barrier 110 with an articulating accordion center 175 which can increase geometric compatibility between different lighthead models and sizes by allowing for articulation in the region where the sterile barrier device interfaces the disposable handle cover 005 or 006. FIG. 4 discloses a feathered center sterile barrier 100 with a feathered edge 180, which can increase geometric compatibility between the sterile barrier and disposable handle covers 005 or 006. FIG. 5 discloses a sterile barrier with an integrated handle cover 115, which can minimize the risk of contaminants breaching the interface between the disposable handle cover 005 or 006, and to minimize the steps needed to prepare the lighthead for a surgical procedure. FIG. 6 discloses a sterile barrier with an integrated camera handle cover 120, wherein the cover may be configured with a region 185 to access lighthead or camera control interfaces disposed thereunder.

Retrofit Kit Compatability

To reduce cost and provide wider cross-compatibility, surgical lightheads 001 can be configured with aftermarket, non-OEM handle cover systems as illustrated in FIGS. 7a, 8a, and 9a. These third-party handle cover systems typically require an adapter (e.g. adapter 009, 007, or 008, respectively), to be removably or separably mounted to the standard surgical lighthead handle 003 or the camera surgical lighthead handle 004 to accept a standardized disposable cover (e.g. 005, 006, 011, or 012) or disposable handle (e.g. 010). The protective barrier device disclosed herein can be adapted to accommodate and/or mount to said adapters with and without the use of disposable covers or handles provided by third-parties. FIGS. 7a, 7b, and 7c disclose a disposable barrier 125 configured to be compatible with camera handle 004 retrofit adapter 009 and disposable rigid camera cover 012. The barrier (e.g. 125, 130, 135, 140) can be conical or partially conical in form to both provide integral geometric stability during mounting and while mounted, and to accommodate the retrofit adapters (e.g. adapter 009, 007, or 008).

With retrofit systems using rigid disposable devices similar to cover 012 or handle 010 (FIGS. 7a and 8a), the sterile barrier 125 or 130 can be attached to said cover and then screwed into a retrofit adapter similar to adapter 007 or 009. Once the surgical procedure is complete, the devices 010 or 012 can be unscrewed, allowing the sterile barrier 125 or 130 to be removed with both the sterile barrier and handle cover being subsequently disposed of. FIG. 7c discloses a disposable barrier 140 with accordion convolutions 175 to accommodate fitment variations between a wider range of lighthead models and sizes.

FIGS. 8a and 8b disclose a disposable barrier 130 configured to be compatible with a disposable rigid retrofit handle 010 and retrofit adapter 007. Similar to the barrier device 125 disclosed above for retrofit camera covers, the barrier 130 can be retained by the disposable handle and the shape of the barrier inherent to the 3-dimensional geometry provides integral stability. Also similar to barrier 125, 130 can also be configured with accordion convolutions 175 to provide a wider range of lighthead compatibility. FIGS. 9a and 9b disclose a disposable barrier 135 configured to be compatible with a disposable flexible retrofit handle adapter 008. This retrofit system is commonly configured with a thin, flexible disposable handle cover 011 (not shown). The barrier device 135 can be retained by the friction at the interface between itself and the flexible handle cover adapter 008. When the light needs to be configured with a sterile barrier, the barrier device 135 can be slid onto cover adapter 008, and then subsequently removed and disposed of to allow for a new sterile barrier 135 to be installed.

As with barrier devices 125 and 130 disclosed above, the shape of barrier 135 can provide integral dimensional stability. The barrier 140 can also be configured with accordion convolutions 175, similar to 125 and 130, to accommodate a wider range of lighthead dimensional variations. These variations include the height of the retrofit adapters (007, 008, or 009) to the face of the surgical lighthead window 002, the diameter of said window, and the shape/size of the lighthead assembly 001. Note in FIGS. 8b and 9b, the barrier may extend beyond the edge of the lighthead to provide additional coverage to the sides of the lighthead assembly 001, auxiliary handles 014, and other exposed surfaces. This extended coverage can act to minimize or prevent contamination of these adjacent surfaces. This extended coverage capability applies to all disposable sterile barriers disclosed herein.

Multi-Layer Peelable Barrier

FIG. 10 discloses a multi-layer, laminated sterile barrier system 200, containing a plurality of layers represented by components or peelably removable layers 205a, 205b, 205c, and 205d. To use this system, multi-layer sterile barrier system 200 can be applied or attached to the surgical lighthead 001 prior to surgical procedures being performed in proximity to the lighthead. When a new sterile barrier is desired, the top layer, illustrated as 205a in FIG. 10 is peeled off (as shown by arrows 400 and 405) via the exposed, angularly staggered peel tab 150, thereby revealing another sterile barrier (assuming there are barriers remaining in the packet or barrier system 200). Following removal, the contaminated sterile barrier component 205 can be disposed of. This procedure can be repeated until all disposable sterile barrier layers (205a, 205b, 205c, and 205d) have been depleted, wherein a new multi-layer sterile barrier packet 200 can be applied to protect the lighthead from biological contamination.

Installation Support Carrier

During installation of the sterile barrier (e.g. 100), surgical lighthead 001 can be oriented in many different positions that are not conducive to low-effort application of a thin, flexible plastic film to the lighthead window 002. FIG. 12 discloses a support device 300 that eases installation by providing geometric stability to the sterile barrier while it is being maneuvered into position on the surgical lighthead. Once the sterile barrier is in position, the support device 300 can be removed. The support device may incorporate a low-tack adhesive or another means to maintain proper orientation between the support carrier and the sterile barrier during positioning.

The sterile barrier device can be similar to a shower-cap for the front of surgical lightheads. Surgical lightheads can be shrink-wrapped onto the surgical lightheads.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination. For example, the center variations, adhesive locations, and attachment methods disclosed may be compatible with many of the sterile barrier configurations disclosed herein. A multitude of other methods of sterile barrier attachment are recognized as being potentially equally effective and possibly superior to those disclosed herein. For example, where adhesives are disclosed, these may be replaceable with a multitude of other attachment means, such as magnets, Velcro, elastic bands, friction, static cling, suction, mechanical fasteners, or a combination thereof.

We claim:

1. A light-transmitting, disposable barrier system comprising:
   a light-emitting region on a surgical lighthead;
   a light transmitting barrier configured to partially cover the light-emitting region on the surgical lighthead;
   at least one of a positioning handle, a camera housing, an attachment point, and a control interface configured to attach the light transmitting barrier to the light-emitting region on the surgical lighthead.

2. The barrier system of claim 1, wherein the light transmitting barrier is configured to be removably attached to the light-emitting region on the surgical lighthead by the at least one of the positioning handle, the camera housing, the attachment point, and the control interface.

3. The barrier system of claim 1, wherein the light transmitting barrier is configured to at least partially cover the at least one of: the positioning handle, the camera housing, the attachment point, and the control interface.

4. A light-transmitting, disposable barrier system comprising:
   a surgical lighthead comprising a light-emitting region;
   a light-transmitting barrier configured to partially cover the light-emitting region; and
   wherein the light-transmitting barrier is comprised of at least one of the following features for providing increased geometric stability to the region of the light-transmitting barrier covering the light-emitting region: a conical form, a stiffening rib, an out-of-plane formed feature, an accordion shape having evenly spaced folds like bellows of an accordion, and a reinforcement member.

5. The barrier system of claim 4, wherein the light-transmitting barrier is configured to be attached to the light-emitting region by at least one of the following: a positioning handle, a camera housing, an attachment point, a disposable cover, and a control interface.

6. The barrier system of claim 4, wherein the light-transmitting barrier is removably adhered to the light-emitting region of the surgical lighthead with at least one of: an adhesive, static cling, and a magnet.

7. A light-transmitting, disposable barrier system comprising:
   a surgical lighthead comprising a light-emitting region; and
   a light-transmitting barrier configured to partially cover the light-emitting region; and
   wherein the region of the light-transmitting barrier configured to cover the light-emitting region is comprised of an accordion shape having evenly spaced folds like bellows of an accordion.

8. The barrier system of claim 7, wherein the light-transmitting barrier is configured to be attached to the light-emitting region of the surgical lighthead by at least one of the following: a positioning handle, a camera housing, an attachment point, an adhesive, static cling, a magnet, a disposable cover, and a control interface.

9. A method for maintaining a sterile surface comprising:
   providing a light-emitting device, wherein the device comprises a light-emitting region;
   providing a first light-transmitting disposable barrier configured to partially cover the light-emitting region;
   providing at least one of a positioning handle, a camera housing, an attachment point, and a control interface;
   attaching the first light-transmitting disposable barrier to the light-emitting region by at least one of the following: the positioning handle, the camera housing, the attachment point, and the control interface;
   removing the first light-transmitting disposable barrier; and
   attaching a second light-transmitting disposable barrier to the light-emitting region.

10. The method of claim 9, wherein the first and second light-transmitting disposable barriers are configured to be removably attached to the light-emitting region by the at least one of the positioning handle, the camera housing, the attachment point, and the control interface removably attached to the surgical lighthead.

11. The method of claim 9, wherein the first and second light-transmitting disposable barriers are configured to at least partially cover at least one of the following: the positioning handle, the camera housing, the attachment point, and the control interface.

* * * * *